(12) United States Patent
Zhao et al.

(10) Patent No.: US 7,160,834 B2
(45) Date of Patent: Jan. 9, 2007

(54) SOLUBLE GROUP-10 α-DIIMINE CATALYST PRECURSORS, CATALYSTS AND METHODS FOR DIMERIZING AND OLIGOMERIZING OLEFINS

(75) Inventors: Baiyi Zhao, Kingwood, TX (US); Kevin R. Squire, Kingwood, TX (US); Smita Kacker, Houston, TX (US); Jo Ann Marie Canich, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 589 days.

(21) Appl. No.: 10/391,421

(22) Filed: Mar. 18, 2003

(65) Prior Publication Data

US 2004/0186010 A1 Sep. 23, 2004

(51) Int. Cl.
*B01J 31/00* (2006.01)
*C07C 2/00* (2006.01)

(52) U.S. Cl. ..................... 502/152; 585/500
(58) Field of Classification Search ................ 502/152; 585/500
See application file for complete search history.

(56) References Cited

U.S. PATENT DOCUMENTS

| | | | |
|---|---|---|---|
| 5,571,881 A | 11/1996 | Goodall et al. | |
| 5,677,405 A | 10/1997 | Goodall et al. | |
| 5,741,869 A | 4/1998 | Goodall et al. | |
| 5,866,663 A | 2/1999 | Brookhart et al. | |
| 5,880,323 A | 3/1999 | Brookhart, III et al. | |
| 6,303,724 B1 | 10/2001 | Goodall et al. | |
| 6,545,108 B1 | 4/2003 | Moody et al. | 526/161 |
| 6,559,091 B1 * | 5/2003 | Moody et al. | 502/167 |
| 6,579,823 B1 * | 6/2003 | Moody et al. | 502/167 |
| 6,706,891 B1 * | 3/2004 | Ponasik et al. | 548/523 |
| 6,767,906 B1 * | 7/2004 | Imbach et al. | 514/234.2 |
| 6,790,579 B1 | 9/2004 | Goodall et al. | |
| 6,825,356 B1 * | 11/2004 | Moody et al. | 548/405 |
| 6,844,446 B1 * | 1/2005 | Moody et al. | 548/523 |
| 6,946,532 B1 * | 9/2005 | Moody et al. | 526/161 |
| 7,002,013 B1 * | 2/2006 | Chi et al. | 546/10 |
| 2004/0039238 A1 | 2/2004 | Zhao et al. | |
| 2004/0044150 A1 | 3/2004 | Zhao et al. | |

FOREIGN PATENT DOCUMENTS

| | | |
|---|---|---|
| DE | 199 44 993 | 3/2001 |
| EP | 0924223 | 12/1998 |
| JP | 63039389 | 2/1988 |
| WO | 00/10945 | 3/2000 |
| WO | WO 00/50470 | 8/2000 |
| WO | WO 01/21586 | 3/2001 |
| WO | 01/83571 | 11/2001 |
| WO | 04/007509 | 1/2004 |

OTHER PUBLICATIONS

Elvers, et al., Ed. Ullmann's Encyclopedia of Industrial Chemistry, vol. A13, VCH Verlagsgesellschaft mbH, Weinheim, 1989, p. 243-247 and 275-276.
Cornils, ET al., Ed., Applied Homogeneous Catalysis with Organometallic Compounds, A Comprehensive Handbook, and vol. 1, VCH Verlagsgesellschaft mbH, Weinheim, 1996, p. 245-258.
B. Elvers, et al., Ed. *Ullmann's Encyclopedia of Industrial Chemistry*, Hydrocarbons, vol. A 13, VCH Verlagsgesellschaft mbH, Weinheim, 1989, pp. 243-247 and 275-276.
B. Cornils, et al., Ed., "Applied Homogeneous Catalysis with Organometallic Compounds", *A Comprehensive Handbook*, vol. 1, VCH Verlagsgesellschaft mbH, Weinheim, 1996, pp. 245-258.
C. Killian, et al., "Preparation of Linear α-Olefins Using Cationic Nickel(II) α-Diimine", *Organometallics*, 1997, 16, pp. 2005-2007.
S. Svejda, et al., "Ethylene Oligomerization and Propylene Dimerization Using Cationic (α-Diimine)nickel(II) Catalysts", *Organometallics*, 1999, 18, pp. 65-74.
Abakumov et al., "Bis(1,4-di-*tert*-butyl-1, 4-diazabutadiene) copper(I)[(3,6-di-*tert*-butyl-o-benzosemiquinono)(3,6-di-*tert*-butylcatecholato)cuprate(II)]. The molecular structure and intramolecular electron transfer", *Russian Chemical Bulletin*, International Edition, vol. 50, No. 11, Nov. 2001, pp. 2193-2199.
Kannan, et al., "Dinuclear diimine palladium (II) and platinum (ii) hydroxo and amido complexes : synthesis and X-ray crystal structures", *Polyhedron* 19 (2000) pp. 155-163.
McCord, et al., "$^{13}$C and 2D NMR Analysis of Propylene Polymers Made with α-Diimine Late Metal Catalysts", *Macromolecules*, 2001, 34, pp. 362-371.
Pappalardo, et al., "Some Evidence of a Dual Stereodifferentation Mechanism in the Polymerization of Propene by α-Diimine Nickel Catalysts", *Macromolecules*, 2000, 33, pp. 9483-9487.
Yang, et al. "Unsymmetrical 1,4-Diazabutadiene Complexes of Platinum (II)", *Organometallics*, 1997, 16, pp. 5234-5243.
Yang, et al. "Dimethyl and Cationic 1,4-Diazabutadiene Complexes of Platinum (II)", *Organometallics*, 1998, 17, pp. 5102-5113.
Benedix, et al. "Electronic Structure and Spectroscopic Properties of Copper Catecholate Complexes with Interligand Charge Transfer Behavior", *Inorganica Chimica Acta*, 1993, 204, pp. 189-193.
Wenzel, et al., "New Indigoid Compounds by Reduction of *Bis*-Imidoylchlorides of Oxalic Acid—A Further Evidence for Dimeric Isocyanides?", *Monatshefte fur Chemie*, 130, 1999, pp. 1373-1382.
Wood, et al., "Synthesis of Polystyrene by Dispersion Polymerization in 1,1,1,2-Tetrafluoroethane (R134a) Using Inexpensive Hydrocarbon Macromonomer Stabilizers", *Macromolecules*, 2003, 36 pp. 7534-7542.

(Continued)

*Primary Examiner*—J. A. Lorengo
*Assistant Examiner*—Elizabeth A. Bolden
(74) *Attorney, Agent, or Firm*—Catherine L. Bell

(57) ABSTRACT

This invention relates to late transition metal catalyst precursors and catalysts for olefin dimerizations and oligomerizations, and to methods for making and using these catalysts.

39 Claims, No Drawings

OTHER PUBLICATIONS

Boussie, et al., "Parallel Solid-Phase Synthesis, Screening, and Encloding Strategies for Olefin-Polymerization Catalysts", Tetrahedron, 55, 1999, pp. 11699-11710.

ACS Registry No. 117869-99-5.

Zhong et al., "C—H Bond Activation by Cationic Platinum(II) Complexes: Ligand Electronic and Steric Effects", J. Am. Chem. Soc., vol. 124, No. 7, 2002, pp. 1378-1399.

Bähr, "Über Schwermetallkomplexe bifunktioneller Schiffscher Basen", Z. Anorg. Allg. Chem. Band, 267, (1951), pp. 137-160.

Drent et al., "Palladium Catalyzed Alternating Copolymerization of Alkenes and Carbon Monoxide", Chem.. Rev. (1996), pp. 663-681.

* cited by examiner

SOLUBLE GROUP-10 α-DIIMINE CATALYST PRECURSORS, CATALYSTS AND METHODS FOR DIMERIZING AND OLIGOMERIZING OLEFINS

TECHNICAL FIELD

This invention relates to late transition metal catalyst precursors and catalysts for olefin dimerizations and oligomerizations, and to methods for making and using these catalysts.

BACKGROUND OF THE INVENTION

Alpha-olefins, especially those containing four to twenty carbon atoms, are important items of commerce. They are used as intermediates in the manufacture of detergents, as monomers (especially in linear low-density polyethylene), and as intermediates for many other types of products. Consequently, improved methods of making these compounds are desired. Especially desired, is a process capable of making a range of linear α-olefins such as 1-butene and 1-hexene?

Most commercially produced α-olefins are made by the oligomerization of ethylene, catalyzed by various types of compounds, see for instance B. Elvers, et al., Ed. Ullmann's Encyclopedia of Industrial Chemistry, Vol. A13, VCH Verlagsgesellschaft mbH, Weinheim, 1989, p. 243–247 and 275–276, and B. Cornils, ET al., Ed., Applied Homogeneous Catalysis with Organometallic Compounds, A Comprehensive Handbook, and Vol. 1, VCH Verlagsgesellschaft mbH, Weinheim, 1996, p. 245–258. The major types of commercially used catalysts are alkylaluminum compounds, certain nickel-phosphine complexes, and a titanium halide with a Lewis acid such as $AlCl_3$. In all of these processes, significant amounts of branched internal olefins and diolefins are produced. As these are undesirable byproducts, catalysts and/or processes that more selectively dimerize and/or oligomerize olefins would be very valuable.

The present inventors have discovered a new genus of catalyst precursors which, when converted into active catalyst is highly selective for the dimerization and oligomerization of α-olefins.

For additional background, see WO 01/21586 and WO 00/50470.

SUMMARY

Invention catalyst systems comprise nickel, platinum or palladium components as the catalyst precursor, and an activator (or "co-catalyst") capable of producing α-olefins in a dimerization and/or oligomerization reaction. The catalyst precursor compounds may be represented by the formula:

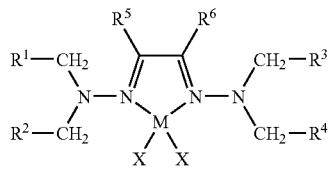

wherein:
(a) N is nitrogen;
(b) C is carbon;
(c) H is hydrogen;
(d) M is a Group-10 metal;
(e) $R^1$, $R^2$, $R^3$ and $R^4$ are independently hydrocarbyl, substituted hydrocarbyl, halocarbyl, or substituted halocarbyl; or $R^1$ and $R^2$ or $R^3$ and $R^4$, independently, are connected to form a heteroalicyclic hydrocarbyl ring structure;
(f) $R^5$ and $R^6$ are, independently, hydrogen, hydrocarbyl radicals, substituted hydrocarbyl, halocarbyl or substituted halocarbyl radicals; or are connected to form a saturated, partially unsaturated or aromatic ring structure provided they do not form a acenaphthene ring structure; and
(g) X are, independently, abstractable ligands.

In any embodiment, the abstractable ligands may be independently one of hydride, hydrocarbyl radicals, or hydrocarbyl-radical-substituted organometalloid radicals. Further, the abstractable ligands may be independently hydride radicals; hydrocarbyl radicals; hydrocarbyl-substituted, or organometalloid radicals. The abstractable ligands may be independently one of chloride, bromide, iodide, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, hydride, phenyl, benzyl, phenethyl, tolyl, methoxy, ethoxy, propoxy, butoxy, dimethylamino, diethylamino, methylethylamino, phenoxy, benzoxy, allyl, 1,1-dimethyl allyl, 2-carboxymethyl allyl, acetylacetonate, 1,1,1,5,5,5-hexa-fluoroacetylacetonate, 1,1,1-trifluoro-acetylacetonate, or 1,1,1-trifluoro-5,5-di-methylacetylacetonate radicals.

In any embodiment, X may independently be one of chloride, bromide, iodide, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, hydride, phenyl, benzyl, phenethyl, tolyl, methoxy, ethoxy, propoxy, butoxy, dimethylamido, diethylamido, methylethylamido, phenoxy, benzoxy, or allyl.

In any embodiment, $R^1$–$R^6$ are independently selected from methyl, ethyl, or all isomers of propyl, butyl, pentyl, hexyl, heptyl, octyl, nonyl, decyl, undecyl, dodecyl, tridecyl, tetradecyl, octacosyl, nonacosyl, triacontyl, cyclohexyl, cyclopentyl, cycloheptyl, cyclooctyl, cyclodecyl, cyclododecyl, naphthyl, phenyl, tolyl, benzyl, and phenethyl radicals.

In any embodiment, $R^1$ may be joined to $R^2$ and $R^3$ may be joined to $R^4$ to form a propan-1,3-diyl, butan-1,4-diyl, pentan-1,5-diyl, hexan-1,6-diyl, heptan-1,7-diyl, octane-1,8-diyl, nonan-1,9-diyl, or decan-1,10-diyl fragment, that forms the respective 1-azacyclohexyl, 1-azacycloheptyl, 1-azacyclooctyl, 1-azacyclononyl, 1-azacyclodecyl, 1-azacycloundecyl, 1-azayclododecyl or 1-azacyclotridecyl substituent.

In any embodiment, $R^5$ and $R^6$ may be hydrogen, methyl, ethyl or propyl.

In any embodiment, $R^5$ may be joined to $R^6$ to form 2,2'-biphenyl, cyclohex-1,2-diyl, cyclopent-1,2-diyl, cyclohept-1,2, diyl, cyclooct-1,2-diyl, cyclonon-1,2-diyl, cyclodec-1,2-diyl, cyclododec-1,2-diyl, dioxan-1,2-diyl, dithian-1,2-diyl, oxathian-1,2-diyl, piperazin-1,2-diyl, morpholin-1,2-diyl, or thiamorpholin-1,2-diyl.

In any embodiment, the catalyst precursor compound may be represented by the formula:

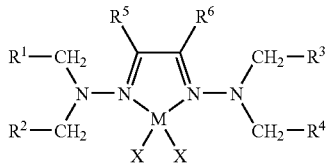

wherein:
(a) N is nitrogen;
(b) C is carbon;
(c) H is hydrogen;
(d) M is nickel or palladium;
(e) $R^1$ is joined to $R^2$ and $R^3$ is joined to $R^4$ to form a heteroalicyclic hydrocarbyl ring structure;
(f) $R^5$ and $R^6$ are independently hydrogen, or a methyl, ethyl or propyl radical; and
(g) X are selected from chloride, bromide, methyl or ethyl.

In one embodiment, the invention is a process for preparing dimers and/or oligomers comprising combining under suitable conditions ethylene, propylene, and/or 1-butene monomer; activator; and one or more catalyst precursor compounds represented by the formula:

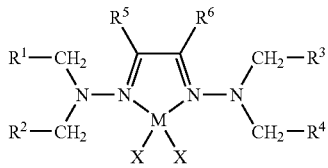

wherein:
(h) N is nitrogen;
(i) C is carbon;
(j) H is hydrogen;
(k) M is a Group-10 metal;
(l) $R^1$, $R^2$, $R^3$ and $R^4$ are independently hydrocarbyl, substituted hydrocarbyl, halocarbyl, or substituted halocarbyl; or $R^1$ and $R^2$ or $R^3$ and $R^4$, independently, are connected to form an heteroalicyclic hydrocarbyl ring structure;
(m) $R^5$ and $R^6$ are independently hydrogen, hydrocarbyl radicals, substituted hydrocarbyl, halocarbyl or substituted halocarbyl radicals; and
(n) X are independently abstractable ligands;

and obtaining therefrom a product comprising one or more of 2 to 75 mer unit oligomers.

In any embodiment of the process, the abstractable ligands may be independently one of hydride, hydrocarbyl radicals, or hydrocarbyl-radical-substituted organometalloid radicals.

In any embodiment of the process, X may independently be one of chloride, bromide, iodide, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, hydride, phenyl, benzyl, phenethyl, tolyl, methoxy, ethoxy, propoxy, butoxy, dimethylamido, diethylamido, methylethylamido, phenoxy, benzoxy, or allyl.

In any embodiment of the process, $R^1$–$R^6$ may independently be selected from methyl, ethyl, or all isomers of propyl, butyl, pentyl, hexyl, heptyl, octyl, nonyl, decyl, undecyl, dodecyl, tridecyl, tetradecyl, octacosyl, nonacosyl, triacontyl, cyclohexyl, cyclopentyl, cycloheptyl, cyclooctyl, cyclodecyl, cyclododecyl, naphthyl, phenyl, tolyl, benzyl, and phenethyl radicals.

In any embodiment of the process, $R^1$ may be joined to $R^2$ and $R^3$ may be joined to $R^4$ to form a propan-1,3-diyl, butan-1,4-diyl, pentan-1,5-diyl, hexan-1,6-diyl, heptan-1,7-diyl, octane-1,8-diyl, nonan-1,9-diyl, or decan-1,10-diyl fragment, that forms the respective 1-azacyclohexyl, 1-azacycloheptyl, 1-azacyclooctyl, 1-azacyclononyl, 1-azacyclodecyl, 1-azacycloundecyl, 1-azayclododecyl or 1-azacyclotridecyl substituent.

In any embodiment of the process, $R^5$ and $R^6$ may be hydrogen, methyl, ethyl, or propyl.

In any embodiment of the process, $R^5$ may be joined to $R^6$ to form or 2,2'-biphenyl, cyclohex-1,2-diyl, cyclopent-1,2-diyl, cyclohept-1,2, diyl, cyclooct-1,2-diyl, cyclonon-1,2-diyl, cyclodec-1,2-diyl, cyclododec-1,2-diyl, dioxan-1,2-diyl, dithian-1,2-diyl, oxathian-1,2-diyl, piperazin-1,2-diyl, morpholin-1,2-diyl, or thiamorpholin-1,2-diyl.

In any embodiment of the process, the abstractable ligands may independently be hydride radicals; hydrocarbyl radicals; hydrocarbyl-substituted, or organometalloid radicals.

In any embodiment of the process, the abstractable ligands may be one of chloride, bromide, iodide, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, hydride, phenyl, benzyl, phenethyl, tolyl, methoxy, ethoxy, propoxy, butoxy, dimethylamino, diethylamino, methylethylamino, phenoxy, benzoxy, allyl, 1,1-dimethyl allyl, 2-carboxymethyl allyl, acetylacetonate, 1,1,1,5,5,5-hexa-fluoroacetylacetonate, 1,1,1-trifluoro-acetylacetonate, or 1,1,1-trifluoro-5,5-di-methylacetylacetonate radicals.

In any embodiment of the process, the monomer may consist essentially of ethylene.

In any embodiment of the process, the product may comprise 2 to 10 mer unit oligomers, 2 to 6 mer unit oligomers and/or 2 to 10 mer unit oligomers.

In any embodiment of the process, the product may comprise greater than 90 weight percent oligomers having 2 to 75 mer units, or 2 to 6 mer units; or the product may comprise greater than 95 weight percent oligomers having 2 to 75 mer units and/or 2 to 6 mer units.

One embodiment of the invention is a process for preparing dimers and/or oligomers comprising combining under suitable conditions ethylene, propylene, and/or 1-butene; activator; and one or more catalyst precursor compounds represented by the formula:

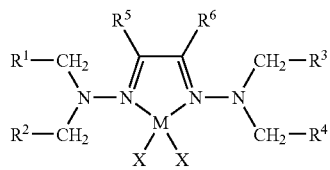

wherein:
(o) N is nitrogen;
(p) C is carbon;
(q) H is hydrogen;
(r) M is nickel or palladium;
(s) $R^1$ is joined to $R^2$ and $R^3$ is joined to $R^4$ to form a heteroalicyclic hydrocarbyl ring structure;
(t) $R^5$ and $R^6$ are independently hydrogen, or a methyl, ethyl or propyl radical; and
(u) X are selected from chloride, bromide methyl or ethyl;

and obtaining therefrom a product consisting essentially of one or more of 2 to 75 mer units oligomers.

In any embodiment of the process, suitable conditions comprise a polymerization pressure of 800 psig or less, 500 psig or less, or 200 psig or less.

Definitions

The term "hydrocarbyl radical" is sometimes used interchangeably with "hydrocarbyl" throughout this document. For purposes of this disclosure, "hydrocarbyl radical" encompasses $C_1$–$C_{50}$ radicals. These radicals can be linear, branched, or cyclic, and when cyclic, aromatic or non-aromatic.

Substituted hydrocarbyl radicals are radicals in which at least one hydrogen atom has been substituted with at least one functional group such as $NR''_2$, $OR''$, $PR''_2$, $SR''$, $BR''_2$, $SiR''_3$, $GeR''_3$ and the like or where at least one non-hydrocarbon atom or group has been inserted within the hydrocarbyl radical, such as O, S, NR'', PR'', BR'', $SiR''_2$, $GeR''_2$, and the like, where R'' is independently a hydrocarbyl or halocarbyl radical. The functional group can be an organometalloid radical.

Halocarbyl radicals are radicals in which one or more hydrocarbyl hydrogen atoms have been substituted with at least one halogen or halogen-containing group (e.g. F, Cl, Br, I).

Substituted halocarbyl radicals are radicals in which at least one hydrocarbyl hydrogen or halogen atom has been substituted with at least one functional group such as $NR''_2$, $OR''$, $PR''_2$, $SR''$, $BR''_2$, $SiR''_3$, $GeR''_3$ and the like or where at least one non-carbon atom or group has been inserted within the halocarbyl radical such as O, S, NR'', PR'', BR'', $SiR''_2$, $GeR''_2$, and the like where R'' is independently a hydrocarbyl or halocarbyl radical provided that at least one halogen atom remains on the original halocarbyl radical. The functional group can be an organometalloid radical.

In some embodiments, the hydrocarbyl radical is independently selected from methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, or triacontynyl isomers. For this disclosure, when a radical is listed it indicates that radical type and all other radicals formed when that radical type is subjected to the substitutions defined above. Alkyl, alkenyl and alkynyl radicals listed include all isomers including where appropriate cyclic isomers, for example, butyl includes n-butyl, 2-methylpropyl, 1-methylpropyl, tert-butyl, and cyclobutyl (and analogous substituted cyclopropyls); pentyl includes n-pentyl, cyclopentyl, 1-methylbutyl, 2-methylbutyl, 3-methylbutyl, 1-ethylpropyl, and neopentyl (and analogous substituted cyclobutyls and cyclopropyls); butenyl includes E and Z forms of 1-butenyl, 2-butenyl, 3-butenyl, 1-methyl-1-propenyl, 1-methyl-2-propenyl, 2-methyl-1-propenyl and 2-methyl-2-propenyl (and cyclobutenyls and substituted cyclopropenyls). Cyclic compound having substitutions include all isomer forms, for example, methylphenyl would include ortho-methylphenyl, meta-methylphenyl and para-methylphenyl; dimethylphenyl would include 2,3-dimethylphenyl, 2,4-dimethylphenyl, 2,5-dimethylphenyl, 2,6-diphenylmethyl, 3,4-dimethylphenyl, and 3,5-dimethylphenyl.

For purposes of this disclosure, oligomers are defined as having about 2–75 mer units. In any of the embodiments described herein, oligomers are produced having from 2–50 mer units, or from 2–25 mer units, or from 2–10 mer units, or from 2–6 mer units, or from 2–4 mer, or from 2–3 mer units. A mer is defined as a unit of an oligomer or polymer that originally corresponded to the olefin that was used in the polymerization reaction. For example, the mer of polyethylene would be ethylene.

Abstractable ligands are ligands that are removed from the catalyst precursor to activate it. They are sometimes assigned the label X in this disclosure. X are, independently, hydride radicals, hydrocarbyl radicals, or hydrocarbyl-substituted organometalloid radicals; or two X's are connected and form a 3-to-50-atom metallacycle ring. Specifically, this metallacycle ring could take the form of a bidentate ligand. A specific example of a ligand in which two Xs are joined is a catecholate ligand as defined below. When Lewis-acid activators such as methylalumoxane, aluminum alkyls, alkylaluminum alkoxides or alkylaluminum halides that are capable of donating an X ligand, as described above, to the transition metal component are used, or when the ionic activator is capable of abstracting X, one or more X, which may optionally be bridged to one another, may additionally be independently selected from a halogen, alkoxide, aryloxide, amide, phosphide or other anionic ligand, provided that the resulting activated catalyst contains as least one M-H or M-C connection in which an olefin can insert.

In some structures throughout this specification the ligand-metal connection is drawn with an arrow indicating that the electrons originally came from the ligand. At other times, connection is shown by drawing a solid line. One of ordinary skill in the art recognizes that these depictions are interchangeable.

Alicyclic rings are aliphatic radicals that have a ring or cyclic structure in which the ring portion may be saturated or unsaturated, but in which the ring portion may not be aromatic. One of ordinary skill in the art recognizes that alicyclic, as defined in this document, is a subset of hydrocarbyl, as defined in this document.

"Heteroalicyclic" rings or ring structures are defined herein to mean those that have a ring or cyclic structure in which the ring portion may be saturated or partially unsaturated, but in which the ring portion may not be aromatic, and where the ring portion further includes one or more heteroatoms, i.e., a non-carbon atom, preferably a Group 15 or 16 element such as nitrogen, phosphorus, sulfur, or selenium, but excluding oxygen.

$C_6F_5$ is pentafluorophenyl or perfluorophenyl.

For purposes of this document, the term "comprising" is interchangeable with "including".

For purposes of this disclosure, "catecholate" or "catecholate ligand" encompasses a ligand comprising a phenyl ring. Two oxygen atoms connect to the phenyl ring at the ring's 1 and 2 positions. The ligand connects to the metal center of the catalyst precursor through both of these oxygen atoms. This leaves four hydrogen atoms connected to the phenyl ring at its 3, 4, 5 and 6 positions. 20, Zero, one, two, three, or four of these hydrogen atoms can be substituted with a $C_1$–$C_{30}$ hydrocarbyl radical. Also, adjacent catecholate hydrocarbyl radicals can join to transform the catecholate into a substituted or unsubstituted, fused-multi-ring system.

DETAILED DESCRIPTION

In one embodiment of this invention, the catalyst precursor can be represented by the following formula:

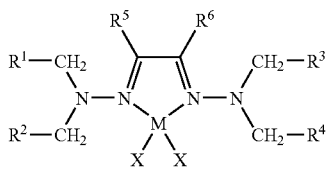

wherein:

N is nitrogen;

C is carbon;

H is hydrogen;

M is a Group-10 metal;

$R^1$, $R^2$, $R^3$ and $R^4$ are independently hydrocarbyl, substituted hydrocarbyl, halocarbyl, or substituted halocarbyl, preferably, a $C_1$ to $C_{30}$ hydrocarbyl, a $C_1$ to $C_{30}$ substituted hydrocarbyl, a $C_1$ to $C_{30}$ halocarbyl, or a $C_1$ to $C_{30}$ substituted halocarbyl, more preferably a $C_1$ to $C_{10}$ hydrocarbyl, a $C_1$ to $C_{10}$ substituted hydrocarbyl, a $C_1$ to $C_{10}$ halocarbyl, or a $C_1$ to $C_{10}$ substituted halocarbyl; or $R^1$ and $R^2$ or $R^3$ and $R^4$, independently, are connected to form an heteroalicyclic hydrocarbyl ring structure;

$R^5$ and $R^6$ are, independently, hydrogen, hydrocarbyl radicals, substituted hydrocarbyl, halocarbyl or substituted halocarbyl radicals, preferably, a $C_1$ to $C_{30}$ hydrocarbyl, a $C_1$ to $C_{30}$ substituted hydrocarbyl, a $C_1$ to $C_{30}$ halocarbyl, or a $C_1$ to $C_{30}$ substituted halocarbyl, more preferably a $C_1$ to $C_{10}$ hydrocarbyl, a $C_1$ to $C_{10}$ substituted hydrocarbyl, a $C_1$ to $C_{10}$ halocarbyl, or a $C_1$ to $C_{10}$ substituted halocarbyl; or $R^5$ and $R^6$ are connected to form a saturated, partially unsaturated or aromatic ring structure provided they do not form a acenaphthene ring structure; and X are, independently, abstractable ligands including hydride, hydrocarbyl, substituted hydrocarbyl, halocarbyl, substituted halocarbyl, or both X groups together are a hydrocarbdiyl, halocarbdiyl, substituted hydrocarbdiyl, or substituted halocarbdiyl; additionally, X may independently be selected from halogen, alkoxide, aryloxide, amide, phosphide, or other anionic ligand when Lewis-acid activators (such as methylalumoxane, aluminum alkyls, alkylaluminum alkoxides or alkylaluminum halides) capable of donating a hydride, hydrocarbyl, substituted hydrocarbyl, halocarbyl or substituted halocarbyl X ligand to the transition metal component are used, or when an ionic activator is capable of abstracting X, provided that the resulting activated catalyst contains as least one M—H or M—C bond into which an olefin can insert.

Examples of specific invention catalyst precursors take the above formula where some components are listed in Table 1. In general, listings in the table include all isomers. When alkyl, alkenyl and alkynyl radicals are disclosed in this application the term includes all isomers and all substitution types, as previously described, unless otherwise stated. When diyls are listed, all isomers are included. For example, propandiyl would include propan-1,2-diyl and propan-1,3-diyl; azabutandiyl would include 1-azabutan-1,4-diyl, 2-azabutan-1,4-diyl, 1-azabutan-1,3-diyl, 2-azabutan-1,3-diyl, 1-azabutan-1,2-diyl, 2-azabutan-1,2-diyl, 1-azabutan-2,3-diyl, 2-azabutan-2,3-diyl, 1-azabutan-2,4-diyl, 2-azabutan-2,4-diyl, 1-azabutan-3,4-diyl, 2-azabutan-3,4-diyl, 2-methyl-2-azapropan-1,3-diyl, and 2-methyl-2-azapropan-1,2-diyl. To illustrate members of the transition metal component, select any combination of the species listed in Table 1. For example, choosing the components in the first row, yields [1,4-bis(diethylamino)-1,4-diaza-1,3-butadiene]nickel dichloride. It should be noted that, for example, when $R^1=R^2=R^3=R^4=$ methyl, the named compound becomes "ethyl" because of the $CH_2$ groups present in the above formula. While the table would name a compound in one way, a more common name may be available. For example, in forming the amine ligand where $R^1$ is joined to $R^2$ and $R^3$ is joined to $R^4$, propan-1,3-diyl with the added $CH_2$'s in the above formula becomes pentan-1,5-diyl and with inclusion of the ring nitrogen atom would become azacyclohexyl, or more commonly piperidene, and the compound, for example, could be named either [1,4-bis(1-azacyclohexyl)-1,4-diaza-1,3-butadiene]nickel dichloride or [1,4-bis(1-piperidenyl)-1,4-diaza-1,3-butadiene]nickel dichloride.

Any combination of components may be selected from the table. The column labeled $R^1$–$R^4$ shows some examples of substituents that can serve as $R^1$–$R^4$. Of course, selecting a particular substituent for $R^1$ is independent of the selection for $R^2$, $R^3$, $R^4$, etc. In other words, the invention allows $R^1=R^2$ or $R^1=R^3$ but does not demand it. Likewise for $R^5$ and $R^6$ and for $X^1$ and $X^2$. $X^1$ and $X^2$ have the same definition as X.

| $R^1, R^2, R^3, R^4$ | $R^5, R^6$ | $X^1, X^2$ | M |
|---|---|---|---|
| methyl | hydrogen | chloride | nickel |
| ethyl | methyl | bromide | palladium |
| propyl | ethyl | iodide | platinum |
| butyl | propyl | methyl | |
| pentyl | butyl | ethyl | |
| hexyl | pentyl | propyl | |
| heptyl | hexyl | butyl | |
| octyl | heptyl | pentyl | |
| nonyl | octyl | hexyl | |
| decyl | nonyl | heptyl | |
| undecyl | decyl | octyl | |
| dodecyl | undecyl | nonyl | |
| tridecyl | dodecyl | decyl | |
| Tetradecyl | tridecyl | undecyl | |
| octacosyl | tetradecyl | dodecyl | |
| Nonacosyl | octacosyl | tridecyl | |
| Triacontyl | nonacosyl | tetradecyl | |
| Cyclohexyl | triacontyl | pentadecyl | |
| Cyclopentyl | cyclohexyl | hexadecyl | |
| Cycloheptyl | cyclopentyl | heptadecyl | |
| Cyclooctyl | cycloheptyl | octadecyl | |
| Cyclodecyl | cyclooctyl | nonadecyl | |
| Cyclododecyl | cyclodecyl | eicosyl | |
| napthyl | cyclododecyl | heneicosyl | |
| phenyl | napthyl | docosyl | |
| tolyl | phenyl | tricosyl | |
| benzyl | tolyl | tetracosyl | |
| phenethyl | benzyl | pentacosyl | |
| Trifluoromethyl | phenethyl | hexacosyl | |
| methoxy | trifluoromethyl | heptacosyl | |
| ethoxy | methoxy | octacosyl | |
| propoxy | ethoxy | nonacosyl | |
| butoxy | propoxy | triacontyl | |
| phenoxy | phenoxy | hydride | |
| Methoxymethyl | methoxymethyl | phenyl | |
| Ethoxymethyl | ethoxymethyl | benzyl | |
| Propoxymethyl | propoxymethyl | phenethyl | |
| Butoxymethyl | butoxymethyl | tolyl | |
| Phenoxymethyl | phenoxymethyl | methoxy | |
| Methylsulfanyl | methylsulfanyl | ethoxy | |
| Ethylsulfanyl | ethylsulfanyl | propoxy | |
| Propylsulfanyl | propylsulfanyl | butoxy | |
| Butylsulfanyl | butylsulfanyl | dimethylamido | |
| Phenylsulfanyl | phenylsulfanyl | diethylamido | |
| Dimethylaminomethyl | dimethylaminomethyl | methylethylamido | |
| Dimethylaminoethyl | dimethylaminoethyl | phenoxy | |
| Diphenylaminomethyl | diphenylaminomethyl | benzoxy | |
| Phenylaminoethyl | phenylaminoethyl | allyl | |
| Methylaminomethyl | methylaminomethyl | 1,1-dimethyl allyl | |
| Dimethylphosphinomethyl | dimethylphosphinomethyl | acetylacetonate | |
| Dimethylphosphinoethyl | dimethylphosphinoethyl | 1,1,1,5,5,5-hexa-fluoroacetylacetonate | |
| Diphenylphosphinomethyl | diphenylphosphinomethyl | 1,1,1-trifluoro-acetylacetonate | |
| Phenylphosphinoethyl | phenylphosphinoethyl | 2-carboxymethyl allyl | |
| Methylphosphinomethyl | methylphosphinomethyl | 1,1,1-trifluoro-5,5-dimethylacetylacetonate | |

| $R^1$ joined to $R^2$, $R^3$ joined to $R^4$ | $R^5$ joined to $R^6$ | $X^1$ joined to $X^2$ |
|---|---|---|
| Propandiyl | 2,2'-biphenyl | methylidene |
| butandiyl | cyclohex-1,2-diyl | ethylidene |
| pentandiyl | cyclopent-1,2-diyl | propylidene |
| hexandiyl | cyclohept-1,2-diyl | tetramethylene |
| Heptandiyl | cyclooct-1,2-diyl | pentamethylene |
| octandiyl | cyclonon-1,2-diyl | hexamethylene |
| nonandiyl | cyclodec-1,2-diyl | butadiene |
| decandiyl | cycloundec-1,2-diyl | methylbutadiene |
| Dodecandiyl | cyclododec-1,2-diyl | dimethylbutadiene |
| Tetradecandiyl | cyclohexen-1,2-diyl | pentadiene |
| Hexadecandiyl | cyclopenten-1,2-diyl | methylpentadiene |
| Octadecandiyl | cyclohepten-1,2-diyl | dimethylpentadiene |
| Azapropandiyl | cycloocten-1,2-diyl | hexadiene |
| Azabutandiyl | cyclononen-1,2-diyl | methylhexadiene |
| Azapentandiyl | cyclodecen-1,2-diyl | dimethylhexadiene |
| Azahexandiyl | cycloundecen-1,2-diyl | catecholate |

-continued

| $R^1$, $R^2$, $R^3$, $R^4$ | $R^5$, $R^6$ | $X^1$, $X^2$ | M |
|---|---|---|---|
| Azaheptandiyl | cyclododecen-1,2-diyl | butylcatecholate | |
| Azaoctandiyl | cyclohexadien-1,2-diyl | diazabutandiyl | |
| Azanonandiyl | dioxan-1,2-diyl | diazapentandiyl | |
| Azadecandiyl | dithian-1,2-diyl | diazahexandiyl | |
| Azadodecandiyl | oxathian-1,2-diyl | dioxabutandiyl | |
| Phosphapropandiyl | piperazin-1,2-diyl | dioxapentandiyl | |
| Phosphabutandiyl | morpholin-1,2-diyl | dioxahexandiyl | |
| Phosphapentandiyl | thiamorpholin-1,2-diyl | | |
| Thiapropandiyl | | | |
| Thiabutandiyl | | | |
| Thiapentandiyl | | | |

Invention catalyst systems can be prepared by combining, in any order, the bidentate ligand,

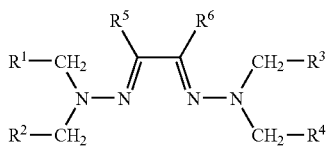

(where N, C, H, $R^1$, $R^2$, $R^3$, $R^4$, $R^5$, and $R^6$ are as previously defined) with a nickel (for example $NiX_2$ or $NiX_2.MeOCH_2CH_2OMe$ where X=Cl, Br, or I), platinum, or palladium halide salt, which may optionally be coordinated by solvent in an activator solution (for example, methylalumoxane dissolved in toluene). All reactants may be added in any order, or even essentially simultaneously.

Mixed catalyst systems can also be used, for example, the invention catalyst can be used in conjunction with a second catalyst in the same reactor or in a series of reactors where the invention catalyst produces ethylene oligomers and the second catalyst incorporates these oligomers into a polymer backbone as a copolymer with ethylene.

Invention polymerization catalyst systems can comprise additional olefin polymerization catalysts. These additional olefin polymerization catalysts are any of those well known in the art to catalyze the olefin to polyolefin reaction. Some invention catalysts systems include Group-4–6 metallocenes as additional olefin polymerization catalysts. Metallocenes include (un)bridged compounds containing one (mono(cyclopentadienyl) metallocenes) or two (bis(cyclopentadienyl) metallocenes) (un)substituted cyclopentadienyl ligand(s). In bridged metallocenes, a single, cyclopentadienyl ligand connects to a heteroatom ligand with both coordinating to the metal center, or two cyclopentadienyl ligands connect together with both cyclopentadienyl ligands coordinating to the metal center. Typical catalysts and their precursors are well known in the art. Suitable description appears in the patent literature, for example U.S. Pat. Nos. 4,871,705, 4,937,299, 5,324,800, EP-A-0418044, EP-A-0591756, WO-A-92/00333 and WO-A-94/01471. Some embodiments select the metallocene compounds from mono- or bis-cyclopentadienyl-substituted, Group-4, -5, and -6 metals in which cyclopentadienyls are (un)substituted with one or more groups or are bridged to each other or to a metal-coordinated heteroatom. Some embodiments select similar metallocene compounds except they are not necessarily bridged to each other or to a metal-coordinated heteroatom. See U.S. Pat. Nos. 5,278,264 and 5,304,614.

Some invention catalysts systems include the following additional olefin polymerization catalysts. Metallocene compounds suitable for linear polyethylene or ethylene-containing copolymer production (where copolymer means, comprising at least two different monomers) are essentially those disclosed in WO-A-92/00333, WO 97/44370 and U.S. Pat. Nos. 5,001,205, 5,057,475, 5,198,401, 5,304,614, 5,308,816 and 5,324,800. Selection of metallocene compounds for isotactic or syndiotactic polypropylene blend production, and their syntheses, are well-known in the patent and academic literature, e.g. *Journal of Organometallic Chemistry* 369, 359–370 (1989). Typically, those catalysts are stereorigid, asymmetric, chiral, or bridged-chiral metallocenes. Invention activators are suited for activating these types of catalyst precursors.

Likewise, some invention catalysts systems include the following additional olefin polymerization catalysts: mono-cyclopentadienyl metallocenes with Group-15 or -16 heteroatoms connected, through a bridging group, to a cyclopentadienyl-ligand ring carbon. Both the cyclopentadienyl Cp-ligand and the heteroatom connect to a transition metal. Some embodiments select a Group-4 transition metal. Additionally, unbridged monocyclopentadienyl, heteroatom-containing Group-4 components of WO 97/22639 will function with this invention. Moreover, transition metal systems with high-oxidation-state, Group-5–10 transition-metal centers are known and can serve as the additional olefin polymerization catalysts with invention catalyst systems.

Invention catalyst systems can use non-cyclopentadienyl, Group-4–5 precursor compounds as the additional olefin polymerization catalysts. Non-cyclopentadienyl, Group-4–5 precursor compounds are activable to stable, discrete cationic complexes include those containing bulky, chelating, diamide ligands, such as described in U.S. Pat. No. 5,318,935 and "Conformationally Rigid Diamide Complexes: Synthesis and Structure of Tantalum (III) Alkyne Derivatives", D. H. McConville, et al, *Organometallics* 1995, 14, 3154–3156. U.S. Pat. No. 5,318,935 describes bridged and unbridged, bis-amido catalyst compounds of Group-4 metals capable of α-olefins polymerization. Bridged bis(arylamido) Group-4 compounds for olefin polymerization are described by D. H. McConville, et al., in *Organometallics* 1995, 14, 5478–5480. Synthetic methods and compound characterization are presented. Further work appearing in D. H. McConville, et al, *Macromolecules* 1996, 29, 5241–5243, describes bridged bis(arylamido) Group-4 compounds that are polymerization catalysts for 1-hexene. Additional invention-suitable transition-metal compounds include those described in WO 96/40805. Cationic Group-3- or Lanthanide olefin polymerization complexes are disclosed in copending U.S. application Ser. No. 09/408,050, filed 29

Sep. 1999, and its equivalent PCT/US99/22690. A monoanionic bidentate ligand and two monoanionic ligands stabilize those catalyst precursors; they are activable with this invention" ionic cocatalysts. Other suitable Group-4–5 non-metallocene catalysts are bimetallocyclic catalyst compounds comprising two independently selected Group-4–5 metal atoms directly linked through two bridging groups to form cyclic compounds.

Invention catalyst systems can use other transition metal catalyst precursors that have a 2+oxidation state as the additional olefin polymerization catalyst. Typical $Ni^{2+}$ and $Pd^{2+}$ complexes are diimines, see "New Pd(II)—and Ni(II)—Based Catalysts for Polymerization of Ethylene and α-Olefins", M. Brookhart, et al, *J. Am. Chem. Soc.*, 1995, 117, 6414–6415, WO 96/23010 and WO 97/02298. See additionally the related bis(imino) Group-8 and -9 organometallic compounds described by V. C. Gibson and others in "Novel olefin polymerization catalysts based on iron and cobalt", *Chem. Commun.*, 849–850, 1998.

For a review of other potential catalysts used in combination or series with the invention catalysts, see S. D. Ittel and L. K. Johnson, Chem. Rev. 2000, 1000, 1169 and V. C. Gibson and S. K. Spitzmesser, Chem. Rev. 2003, 103, 283.

Common activators are useful with this invention: alumoxanes, such as methylalumoxane, modified methylalumoxane, ethylalumoxane and the like; aluminum alkyls such as trimethyl aluminum, triethyl aluminum, triisopropyl aluminum and the like; alkyl aluminum halides such as diethyl aluminum chloride and the like; and alkylaluminum alkoxides.

The alumoxane component useful as an activator typically is an oligomeric aluminum compound represented by the general formula $(R''-Al-O)_n$, which is a cyclic compound, or $R''(R''-Al-O)_n AlR''_2$, which is a linear compound. In the general alumoxane formula, R" is independently a $C_1-C_{20}$ alkyl radical, for example, methyl, ethyl, propyl, butyl, pentyl, isomers thereof, and the like, and "n" is an integer from 1–50. Most preferably, R" is methyl and "n" is at least 4. Methylalumoxane and modified methylalumoxanes are most preferred. For further descriptions see, EP 279586, EP 561476, WO94/10180 and U.S. Pat. Nos. 4,665,208, 4,908,463, 4,924,018, 4,952,540, 4,968,827, 5,041,584, 5,103,031, 5,157,137, 5,235,081, 5,248,801, 5,329,032, 5,391,793, and 5,416,229.

The aluminum alkyl component useful as an activator is represented by the general formula $R''AlZ_2$ where R" is defined above, and each Z is independently R" or a different univalent anionic ligand such as halogen (Cl, Br, I), alkoxide (OR") and the like. Most preferred aluminum alkyls include triethylaluminum, diethylaluminum chloride, triisobutylaluminum, tri-n-octylaluminum and the like.

When alumoxane or aluminum alkyl activators are used, the catalyst-precursor-to-activator molar ratio is from about 1:1000 to 10:1; alternatively, 1:500 to 1:1; or 1:300 to 1:10.

Ionic activators may be used in the practice of this invention. Preferably, discrete ionic activators such as $[Me_2PhNH][B(C_6F_5)_4]$, $[Bu_3NH][BF_4]$, $[NH_4][PF_6]$, $[NH_4][SbF_6]$, $[NH_4][AsF_6]$, $[NH_4][B(C_6H_5)_4]$ or Lewis acidic activators such as $B(C_6F_5)_3$ or $B(C_6H_5)_3$ can be used if they are used in conjunction with a compound capable of alkylating the metal such as an alumoxane or aluminum alkyl, or if in the pre-catalyst, X is a hydride, hydrocarbyl, substituted hydrocarbyl, halocarbyl, substituted halocarbyl.

It is within the scope of this invention to use an ionizing or stoichiometric activator, neutral or ionic, such as tri(n-butyl)ammonium tetrakis (pentafluorophenyl)boron, a trisperfluorophenyl boron metalloid precursor or a trisperfluoronaphtyl boron metalloid precursor, polyhalogenated heteroborane anions (WO 98/43983), boric acid (U.S. Pat. No. 5,942,459) or combination thereof. It is also within the scope of this invention to use neutral or ionic activators alone or in combination with alumoxane or modified alumoxane activators.

Examples of neutral stoichiometric activators include tri-substituted boron, tellurium, aluminum, gallium and indium or mixtures thereof. The three substituent groups are each independently selected from alkyls, alkenyls, halogen, substituted alkyls, aryls, arylhalides, alkoxy and halides. Preferably, the three groups are independently selected from halogen, mono or multicyclic (including halosubstituted) aryls, alkyls, and alkenyl compounds and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). More preferably, the three groups are alkyls having 1 to 4 carbon groups, phenyl, napthyl or mixtures thereof. Even more preferably, the three groups are halogenated, preferably fluorinated, aryl groups. Most preferably, the neutral stoichiometric activator is trisperfluorophenyl boron or trisperfluoronapthyl boron.

Ionic stoichiometric activator compounds may contain an active proton, or some other cation associated with, but not coordinated to, or only loosely coordinated to, the remaining ion of the ionizing compound. Such compounds and the like are described in European publications EP-A-0 570 982, EP-A-0 520 732, EP-A-0 495 375, EP-B1-0 500 944, EP-A-0 277 003 and EP-A-0 277 004, and U.S. Pat. Nos. 5,153,157, 5,198,401, 5,066,741, 5,206,197, 5,241,025, 5,384,299 and 5,502,124 and U.S. patent application Ser. No. 08/285,380, filed Aug. 3, 1994, all of which are herein fully incorporated by reference.

Ionic catalysts can be preparedly reacting a transition metal compound with some neutral Lewis acids, such as $B(C_6F_6)_3$, which upon reaction with the hydrolyzable ligand (X) of the transition metal compound forms an anion, such as $([B(C_6F_5)_3(X)]^-)$, which stabilizes the cationic transition metal species generated by the reaction. The catalysts can be, and preferably are, prepared with activator components which are ionic compounds or compositions. However preparation of activators utilizing neutral compounds is also contemplated by this invention.

Compounds useful as an activator component in the preparation of the ionic catalyst systems used in the process of this invention comprise a cation, which is preferably a Bronsted acid capable of donating a proton, and a compatible non-coordinating anion which anion is relatively large (bulky), capable of stabilizing the active catalyst species (the Group 4 cation) which is formed when the two compounds are combined and said anion will be sufficiently labile to be displaced by olefinic diolefinic and acetylenically unsaturated substrates or other neutral Lewis bases such as ethers, nitrites and the like. Two classes of compatible non-coordinating anions have been disclosed in EPA 277,003 and EPA 277,004 published 1988: 1) anionic coordination complexes comprising a plurality of lipophilic radicals covalently coordinated to and shielding a central charge-bearing metal or metalloid core, and 2) anions comprising a plurality of boron atoms such as carboranes, metallacarboranes and boranes.

In a preferred embodiment, the stoichiometric activators include a cation and an anion component, and may be represented by the following formula:

$$(L^*-H)_d^+ (A^{d-}) \tag{14}$$

wherein L* is an neutral Lewis base;
H is hydrogen;
(L*-H)+ is a Bronsted acid
$A^{d-}$ is a non-coordinating anion having the charge d–
d is an integer from 1 to 3.

The cation component, $(L^*-H)_d^+$ may include Bronsted acids such as protons or protonated Lewis bases or reducible Lewis acids capable of protonating or abstracting a moiety, such as an alkyl or aryl, from the bulky ligand metallocene containing transition metal catalyst precursor, resulting in a cationic transition metal species.

The activating cation $(L^*-H)_d^+$ may be a Bronsted acid, capable of donating a proton to the transition metal catalytic precursor resulting in a transition metal cation, including ammoniums, oxoniums, phosphoniums, silyliums, and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxomiuns from ethers such as dimethyl ether diethyl ether, tetrahydrofuran and dioxane, sulfoniums from thioethers, such as diethyl thioethers and tetrahydrothiophene, and mixtures thereof. The activating cation $(L-H)_d^+$ may also be a moiety such as silver, tropylium, carbeniums, ferroceniums and mixtures, preferably carboniums and ferroceniums. Most preferably $(L^*-H)_d^+$ is triphenyl carbonium.

The anion component $A^{d-}$ include those having the formula $[M^{k+Q}{}_n]^{d-}$ wherein k is an integer from 1 to 3; n is an integer from 2–6; n–k=d; M is an element selected from Group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than 1 occurrence is Q a halide. Preferably, each Q is a fluorinated hydrocarbyl group having 1 to 20 carbon atoms, more preferably each Q is a fluorinated aryl group, and most preferably each Q is a pentafluoryl aryl group. Examples of suitable $A^{d-}$ also include diboron compounds as disclosed in U.S. Pat. No. 5,447,895, which is fully incorporated herein by reference.

Illustrative, but not limiting examples of boron compounds which may be used as an activating cocatalyst in the preparation of the improved catalysts of this invention are tri-substituted ammonium salts such as: trimethylammonium tetraphenylborate, triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, tropillium tetraphenylborate, triphenylcarbenium tetraphenylborate, triphenylphosphonium tetraphenylborate triethylsilylium tetraphenylborate, benzene(diazonium)tetraphenylborate, trimethylammonium tetrakis(pentafluorophenyl)borate, triethylammonium tetrakis(pentafluorophenyl)borate, tripropylammonium tetrakis (pentafluorophenyl)borate, tri(n-butyl)ammonium tetrakis (pentafluorophenyl)borate, tri(sec-butyl)ammonium tetrakis (pentafluorophenyl)borate, N,N-dimethylanilinium tetrakis (pentafluorophenyl)borate, N,N-diethylanilinium tetrakis (pentafluorophenyl)borate, N,N-dimethyl-(2,4,6-trimethylanilinium) tetrakis(pentafluorophenyl)borate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene (diazonium)tetrakis(pentafluorophenyl)borate, trimethylammonium tetrakis-(2,3,4,6-tetrailuorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl(t-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2, 4,6-trimethylanilinium)tetrakis-(2,3,4,6-tetrafluorophenyl) borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium)tetrakis-(2,3,4,6-tetrafluorophenyl)borate, trimethylammonium tetrakis (perfluoronapthyl)borate, triethylammonium tetrakis (perfluoronapthyl)borate, tripropylammonium tetrakis (perfluoronapthyl)borate, tri(n-butyl)ammonium tetrakis (perfluoronapthyl)borate, tri(t-butyl)ammonium tetrakis (perfluoronapthyl)borate, N,N-dimethylanilinium tetrakis (perfluoronapthyl)borate, N,N-diethylanilinium tetrakis (perfluoronapthyl)borate, N,N-dimethyl-(2,4,6-trimethylanilinium)tetrakis(perfluoronapthyl)borate, tropillium tetrakis(perfluoronapthyl)borate, triphenylcarbenium tetrakis(perfluoronapthyl)borate, triphenylphosphonium tetrakis(perfluoronapthyl)borate, triethylsilylium tetrakis(perfluoronapthyl)borate, benzene(diazonium)tetrakis (perfluoronapthyl)borate, trimethylammonium tetrakis (perfluorobiphenyl)borate, triethylammonium, tetrakis (perfluorobiphenyl)borate, tripropylammonium tetrakis (perfluorobiphenyl)borate, tri(n-butyl)ammonium tetrakis (perfluorobiphenyl)borate, tri(t-butyl)ammonium tetrakis (perfluorobiphenyl)borate, N,N-dimethylanilinium tetrakis (perfluorobiphenyl)borate, N,N-diethylanilinium tetrakis (perfluorobiphenyl)borate, N,N-dimethyl-(2,4,6-trimethylanilinium) tetrakis(perfluorobiphenyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene (diazonium)tetrakis(perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis (trifluoromethyl)phenyl)borate, tri(n-butyl)ammonium tetrakis(3,5-bis(trifluoromethyl)phenyl)borate, tri(t-butyl) ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis(trifluoromethyl) phenyl)borate, tropillium tetrakis(3,5-bis(trifluoromethyl) phenyl)borate, triphenylcarbenium tetrakis(3,5-bis (trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, benzene(diazonium)tetrakis(3,5-bis(trifluoromethyl)phenyl)borate, and dialkyl ammonium salts such as: di-(i-propyl)ammonium tetrakis(pentafluorophenyl)borate, and dicyclohexylammonium tetrakis(pentafluorophenyl)borate; and additional tri-substituted phosphonium salts such as tri(o-tolyl)phosphonium tetrakis(pentafluorophenyl)borate, and tri(2,6-dimethylphenyl)phosphonium tetrakis(pentafluorophenyl)borate.

Most preferably, the ionic stoichiometric activator $(L^*\text{-}H)_d^+ (A^{d-})$ is N,N-dimethylanilinium tetrakis(perfluorophenyl)borate, N,N-dimethylanilinium tetrakis(perfluoronapthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronapthyl)borate, triphenylcarbenium tetrakis(perfluorobiphenyl)borate, triphenylcarbenium tetrakis(3,5-bis(trifluoromethyl)phenyl)borate, or triphenylcarbenium tetra(perfluorophenyl)borate.

In one embodiment, an activation method using ionizing ionic compounds not containing an active proton but capable of producing a bulky ligand metallocene catalyst cation and their non-coordinating anion are also contemplated, and are described in EP-A-0 426 637, EP-A-0 573 403 and U.S. Pat. No. 5,387,568, which are all herein incorporated by reference.

Invention catalyst precursors can also be activated with cocatalysts or activators that comprise non-coordinating anions containing metalloid-free cyclopentadienide ions. These are described in U.S. Patent Publication 2002/0058765 A1, published on 16 May 2002.

The term "non-coordinating anion" (NCA) means an anion which either does not coordinate to said cation or which is only weakly coordinated to said cation thereby remaining sufficiently labile to be displaced by a neutral Lewis base. "Compatible" non-coordinating anions are those which are not degraded to neutrality when the initially formed complex decomposes. Further, the anion will not transfer an anionic substituent or fragment to the cation so as to cause it to form a neutral four coordinate metallocene compound and a neutral by-product from the anion. Non-coordinating anions useful in accordance with this invention are those that are compatible, stabilize the metallocene cation in the sense of balancing its ionic charge at +1, yet retain sufficient lability to permit displacement by an ethylenically or acetylenically unsaturated monomer during polymerization. These types of cocatalysts sometimes use tri-isobutyl aluminum or tri-octyl aluminum as a scavenger.

Invention process also can employ cocatalyst compounds or activator compounds that are initially neutral Lewis acids but form a cationic metal complex and a noncoordinating anion, or a zwitterionic complex upon reaction with the invention compounds. For example, tris(pentafluorophenyl) boron or aluminum act to abstract a hydrocarbyl or hydride ligand to yield an invention cationic metal complex and stabilizing noncoordinating anion, see EP-A-0 427 697 and EP-A-0 520 732 for illustrations of analogous Group-4 metallocene compounds. Also, see the methods and compounds of EP-A-0 495 375. For formation of zwitterionic complexes using analogous Group 4 compounds, see U.S. Pat. Nos. 5,624,878; 5,486,632; and 5,527,929.

When the cations of noncoordinating anion precursors are Bronsted acids such as protons or protonated Lewis bases (excluding water), or reducible Lewis acids such as ferrocenium or silver cations, or alkali or alkaline earth metal cations such as those of sodium, magnesium or lithium, the catalyst-precursor-to-activator molar ratio may be any ratio. Combinations of the described activator compounds may also be used for activation. For example, tris(perfluorophenyl)boron can be used with methylalumoxane.

When an ionic activator is used, the catalyst-precursor-to-activator molar ratio is from 1:10 to 1.2:1; 1:10 to 10:1; 1:10 to 2:1; 1:10 to 3:1; 1:10 to 5:1; 1:2 to 1.2:1; 1:2 to 10:1; 1:2 to 2:1; 1:2 to 3:1; 1:2 to 5:1; 1:3 to 1.2:1; 1:3 to 10:1; 1:3 to 2:1; 1:3 to 3:1; 1:3 to 5:1; 1:5 to 1.2:1; 1:5 to 10:1; 1:5 to 2:1; 1:5 to 3:1; 1:5 to 5:1.

The catalyst-precursor-to-alkylating-agent molar ratio is from 1:100 to 100:1; 1:50 to 50:1; 1:10 to 10:1; 1:10 to 2:1; 1:10 to 25:1; 1:10 to 3:1; 1:10 to 5:1; 1:2 to 10:1; 1:2 to 2:1; 1:2 to 25:1; 1:2 to 3:1; 1:2 to 5:1; 1:25 to 10:1; 1:25 to 2:1; 1:25 to 25:1; 1:25 to 3:1; 1:25 to 5:1; 1:3 to 10:1; 1:3 to 2:1; 1:3 to 25:1; 1:3 to 3:1; 1:3 to 5:1; 1:5 to 10:1; 1:5 to 2:1; 1:5 to 25:1; 1:5 to 3:1; 1:5 to 5:1.

Preferred activators include methylalumoxane, modified methylalumoxane, and mixtures of methylalumoxane with dimethylanilinium tetrakis(pentafluorophenyl)borate or tris(pentafluorophenyl)boron.

Invention catalyst precursor solubility allows for the ready preparation of supported catalysts. To prepare uniform supported catalysts, the catalyst precursor should significantly dissolve in the chosen solvent. The term "uniform supported catalyst" means that the catalyst precursor or the activated catalyst approach uniform distribution upon the support's accessible surface area, including the interior pore surfaces of porous supports.

Invention supported catalyst systems may be prepared by any method effective to support other coordination catalyst systems, effective meaning that the catalyst so prepared can be used for oligomerizing olefin in a heterogeneous process. The catalyst precursor, activator, suitable solvent, and support may be added in any order or simultaneously. In one invention embodiment, the activator, dissolved in an appropriate solvent such as toluene is stirred with the support material for 1 minute to 10 hours. The total volume of the activation solution may be greater than the pore volume of the support, but some embodiments limit the total solution volume below that needed to form a gel or slurry (about 100–200% of the pore volume). The mixture is optionally heated to 30–200° C. during this time. The catalyst can be added to this mixture as a solid, if a suitable solvent is employed in the previous step, or as a solution. Or alternatively, this mixture can be filtered, and the resulting solid mixed with a catalyst precursor solution. Similarly, the mixture may be vacuum dried and mixed with a catalyst precursor solution. The resulting catalyst mixture is then stirred for 1 minute to 10 hours, and the catalyst is either filtered from the solution and vacuum dried, or vacuum or evaporation alone removes the solvent.

In another invention embodiment, the catalyst precursor and activator are combined in solvent to form a solution. The support is then added to this solution and the mixture is stirred for 1 minute to 10 hours. The total volume of this solution may be greater than the pore volume of the support, but some embodiments limit the total solution volume below that needed to form a gel or slurry (about 100–200% pore volume). The residual solvent is then removed under vacuum, typically at ambient temperature and over 10–16 hours. But greater or lesser times are possible.

The catalyst precursor may also be supported in the absence of the activator, in which case the activator is added to the liquid phase of a slurry process. For example, a solution of catalyst precursor is mixed with a support material for a period of about 1 minute to 10 hours. The resulting catalyst precursor mixture is then filtered from the solution and dried under vacuum, or vacuum or evaporation alone removes the solvent. The total volume of the catalyst precursor solution may be greater than the pore volume of the support, but some embodiments limit the total solution volume below that needed to form a gel or slurry (about 100–200% of the pore volume).

Additionally, two or more different catalyst precursors may be placed on the same support using any of the support methods disclosed above. Likewise, two or more activators may be placed on the same support.

Suitable solid particle supports typically comprise polymeric or refractory oxide materials. Some embodiments select porous supports (such as for example, talc, inorganic oxides, inorganic chlorides (magnesium chloride)) that have an average particle size greater than 10 µm. Some embodiments select inorganic oxide materials as the support material including Group-2, -3, -4, -5, -13, or -14 metal or metalloid oxides. Some embodiments select the catalyst support materials to include silica, alumina, silica-alumina, and their mixtures. Other inorganic oxides may serve either alone or in combination with the silica, alumina, or silica-alumina. These are magnesia, titania, zirconia, and the like. Lewis acidic materials such as montmorillonite and similar clays may also serve as a support. In this case, the support can optionally double as the activator component. But additional activator may also be used.

As is well know in the art, the support material may be pretreated by any number of methods. For example, inorganic oxides may be calcined, and/or chemically treated with dehydroxylating agents such as aluminum alkyls and the like.

Some embodiments select the carrier of invention catalysts to have a surface area of 10–700 m$^2$/g, or pore volume of 0.1–4.0 cc/g, and average particle size from 10–500 µm. But greater or lesser values may also be used.

Invention catalysts may generally be deposited on the support at a loading level of 10–100 micromoles of catalyst precursor per gram of solid support; alternately from 20–80 micromoles of catalyst precursor per gram of solid support; or from 40–60 micromoles of catalyst precursor per gram of support. But greater or lesser values may be used. Some embodiments select greater or lesser values, but require that the total amount of solid catalyst precursor does not exceed the support's pore volume.

Additionally, oxidizing agents may be added to the supported or unsupported catalyst as described in WO 01/68725.

Process

In the invention dimerization and oligomerization processes, the process temperature may be −100° C. to 300° C., −20° C. to 200° C., or 0° C. to 150° C. Some embodiments select ethylene oligomerization pressures (gauge) from 0 kPa–35 MPa or 500 kPa–15 MPa. While large pressure ranges are possible, for some catalysts, those pressures at or below 800 psig (5,515 kPa) tend to produce dimers and trimers more selectively. In some embodiments of the invention, the reaction ethylene pressure (gauge) is carried out at 800 psig (5,515 kPa) or below; or 500 psig (3,447 kPa) or below; or 200 psig (1,379 kPa) or below; or 100 psig (689 kPa) or below.

The preferred and primary feedstock for the process is the α-olefin, ethylene. But other α-olefins, including but not limited to propylene and 1-butene, may also be used alone or combined with ethylene.

Invention processes may be run in the presence of various liquids, particularly aprotic organic liquids. The homogeneous catalyst system, ethylene, α-olefins, and product are soluble in these liquids. A supported (heterogeneous) catalyst system may also be used, but will form a slurry rather than a solution. Suitable liquids for both homo- and heterogeneous catalyst systems, include alkanes, alkenes, cycloalkanes, selected halogenated hydrocarbons, aromatic hydrocarbons, and in some cases, hydrofluorocarbons. Useful solvents specifically include hexane, toluene, cyclohexane, and benzene.

Also, mixtures of α-olefins containing desirable numbers of carbon atoms may be obtained. Factor K from the Schulz-Flory theory (see for instance B. Elvers, et al., Ed. Ullmann's Encyclopedia of Industrial Chemistry, Vol. A13, VCH Verlagsgesellschaft mbH, Weinheim, 1989, p. 243–247 and 275–276) serves as a measure of these α-olefins' molecular weights. From this theory, $K = n(C_{n+2} \text{ olefin})/n(C_n \text{ olefin})$ where n($C_n$ olefin) is the number of moles of olefin containing n carbon atoms, and n($C_{n+2}$ olefin) is the number of moles of olefin containing n+2 carbon atoms, or in other words the next higher oligomer of $C_n$ olefin. From this can be determined the weight (mass) fractions of the various olefins in the resulting product. The ability to vary this factor provides the ability to choose the then-desired olefins.

Invention-made α-olefins may be further polymerized with other olefins to form polyolefins, especially linear low-density polyethylenes, which are copolymers containing ethylene. They may also be homopolymerized. These polymers may be made by a number of known methods, such as Ziegler-Natta-type polymerization, metallocene catalyzed polymerization, and other methods, see for instance WO 96/23010, see for instance Angew. Chem., Int. Ed. Engl., vol. 34, p. 1143–1170 (1995); European Patent Application, 416,815; and U.S. Pat. No. 5,198,401 for information about metallocene-type catalysts, and J. Boor Jr., Ziegler-Natta Catalysts and Polymerizations, Academic Press, New York, 1979 and G. Allen, et al., Ed., Comprehensive Polymer Science, Vol. 4, Pergamon Press, Oxford, 1989, pp. 1–108, 409–412 and 533–584, for information about Ziegler-Natta-type catalysts, and H. Mark, et al., Ed., Encyclopedia of Polymer Science and Engineering, Vol. 6, John Wiley & Sons, New York, 1992, p. 383–522, for information about polyethylene.

Invention-made α-olefins may be converted to alcohols by known processes, these alcohols being useful for a variety of applications such as intermediates for detergents or plasticizers. The α-olefins may be converted to alcohols by a variety of processes, such as the oxo process followed by hydrogenation, or by a modified, single-step oxo process (the modified Shell process), see for instance B. Elvers, et al., Ed., Ullmann's Encyclopedia of Chemical Technology, 5th Ed., Vol. A18, VCH Verlagsgesellschaft mbH, Weinheim, 1991, p. 321–327.

A set of exemplary catalyst precursors is set out below. These are by way of example only and are not intended to list every catalyst precursor that is within the scope of the invention.

Examples of compounds with symmetrical ligand structures containing saturated heteroalicyclic ring structures include:

1,4-bis(azacyclopent-1-yl)-1,4-diaza-1,3-butadiene]nickel dichloride (1,4-bis(pyrrolidin-1-yl)-1,4-diaza-1,3-butadiene]nickel dichloride), 1,4-bis(azacyclohex-1-yl)-1,4-diaza-1,3-butadiene]nickel dichloride (1,4-bis(piperidin-1-yl)-1,4-diaza-1,3-butadiene]nickel dichloride), 1,4-bis(azacyclohept-1-yl)-1,4-diaza-1,3-butadiene]nickel dichloride (1,4-bis(homopiperidin-1-yl)-1,4-diaza-1,3-butadiene]nickel dichloride), 1,4-bis(azacycloocta-1-yl)-1,4-diaza-1,3-butadiene]nickel dichloride, 1,4-bis(azacyclonon-1-yl)-1,4-diaza-1,3-butadiene]nickel dichloride,
1,4-bis(azacyclodec-1-yl)-1,4-diaza-1,3-butadiene]nickel dichloride,
1,4-bis(azacycloundec-1-yl)-1,4-diaza-1,3-butadiene]nickel dichloride,
1,4-bis(azacyclododec-1-yl)-1,4-diaza-1,3-butadiene]nickel dichloride,
1,4-bis(azacyclotetradec-1-yl)-1,4-diaza-1,3-butadiene] nickel dichloride,
1,4-bis(azacyclohexadec-1-yl)-1,4-diaza-1,3-butadiene] nickel dichloride,
1,4-bis(azacyclooctadec-1-yl)-1,4-diaza-1,3-butadiene] nickel dichloride,
1,4-bis(imidazolidin-1-yl)-1,4-diaza-1,3-butadiene]nickel dichloride,
1,4-bis(piperazin-1-yl)-1,4-diaza-1,3-butadiene]nickel dichloride,
1,4-bis(pyrazolidin-1-yl)-1,4-diaza-1,3-butadiene]nickel dichloride,
1,4-bis(azacyclopent-1-yl)-2,3-dimethyl-1,4-diaza-1,3-butadiene]nickel dichloride (1,4-bis(pyrrolidin-1-yl)-2,3-dimethyl-1,4-diaza-1,3-butadiene]nickel dichloride),
1,4-bis(azacyclohex-1-yl)-2,3-dimethyl-1,4-diaza-1,3-butadiene]nickel dichloride (1,4-bis(piperidin-1-yl)-2,3-dimethyl-1,4-diaza-1,3-butadiene]nickel dichloride),
1,4-bis(azacyclohept-1-yl)-2,3-dimethyl-1,4-diaza-1,3-butadiene]nickel dichloride (1,4-bis(homopiperidin-1-yl)-2,3-dimethyl-1,4-diaza-1,3-butadiene]nickel dichloride),
1,4-bis(azacyclooct-1-yl)-2,3-dimethyl-1,4-diaza-1,3-butadiene]nickel dichloride,
1,4-bis(azacyclonon-1-yl)-2,3-dimethyl-1,4-diaza-1,3-butadiene]nickel dichloride,
1,4-bis(azacyclodec-1-yl)-2,3-dimethyl-1,4-diaza-1,3-butadiene]nickel dichloride,
1,4-bis(azacycloundec-1-yl)-2,3-dimethyl-1,4-diaza-1,3-butadiene]nickel dichloride,
1,4-bis(azacyclododec-1-yl)-2,3-dimethyl-1,4-diaza-1,3-butadiene]nickel dichloride,
1,4-bis(azacyclotetradec-1-yl)-2,3-dimethyl-1,4-diaza-1,3-butadiene]nickel dichloride,
1,4-bis(azacyclohexadec-1-yl)-2,3-dimethyl-1,4-diaza-1,3-butadiene]nickel dichloride,
1,4-bis(azacyclooctadec-1-yl)-2,3-dimethyl-1,4-diaza-1,3-butadiene]nickel dichloride,
1,4-bis(imidazolidin-1-yl)-2,3-dimethyl-1,4-diaza-1,3-butadiene]nickel dichloride,
1,4-bis(piperazin-1-yl)-2,3-dimethyl-1,4-diaza-1,3-butadiene]nickel dichloride,
1,4-bis(pyrazolidin-1-yl)-2,3-dimethyl-1,4-diaza-1,3-butadiene]nickel dichloride,
1,4-bis(azacyclopent-1-yl)-2,3-diethyl-1,4-diaza-1,3-butadiene]nickel dichloride (1,4-bis(pyrrolidin-1-yl)-2,3-diethyl-1,4-diaza-1,3-butadiene]nickel dichloride),
1,4-bis(azacyclohex-1-yl)-2,3-diethyl-1,4-diaza-1,3-butadiene]nickel dichloride (1,4-bis(piperidin-1-yl)-2,3-diethyl-1,4-diaza-1,3-butadiene]nickel dichloride),
1,4-bis(azacyclohept-1-yl)-2,3-diethyl-1,4-diaza-1,3-butadiene]nickel dichloride (1,4-bis(homopiperidin-1-yl)-2,3-diethyl-1,4-diaza-1,3-butadiene]nickel dichloride),
1,4-bis(azacyclooct-1-yl)-2,3-diethyl-1,4-diaza-1,3-butadiene]nickel dichloride,
1,4-bis(azacyclonon-1-yl)-2,3-diethyl-1,4-diaza-1,3-butadiene]nickel dichloride,
1,4-bis(azacyclodec-1-yl)-2,3-diethyl-1,4-diaza-1,3-butadiene]nickel dichloride,
1,4-bis(azacycloundec-1-yl)-2,3-diethyl-1,4-diaza-1,3-butadiene]nickel dichloride,
1,4-bis(azacyclododec-1-yl)-2,3-diethyl-1,4-diaza-1,3-butadiene]nickel dichloride,
1,4-bis(azacyclotetradec-1-yl)-2,3-diethyl-1,4-diaza-1,3-butadiene]nickel dichloride,
1,4-bis(azacyclohexadec-1-yl)-2,3-dimethyl-1,4-diaza-1,3-butadiene]nickel dichloride,
1,4-bis(azacyclooctadec-1-yl)-2,3-diethyl-1,4-diaza-1,3-butadiene]nickel dichloride,
1,4-bis(imidazolidin-1-yl)-2,3-diethyl-1,4-diaza-1,3-butadiene]nickel dichloride,
1,4-bis(piperazin-1-yl)-2,3-diethyl-1,4-diaza-1,3-butadiene] nickel dichloride,
1,4-bis(pyrazolidin-1-yl)-2,3-diethyl-1,4-diaza-1,3-butadiene]nickel dichloride,
1,4-bis(azacyclopent-1-yl)-2-methyl-3-propyl-1,4-diaza-1,3-butadiene]nickel dichloride (1,4-bis(pyrrolidin-1-yl)-2-methyl-3-propyl-1,4-diaza-1,3-butadiene]nickel dichloride),
1,4-bis(azacyclohex-1-yl)-2-methyl-3-propyl-1,4-diaza-1,3-butadiene]nickel dichloride (1,4-bis(piperidin-1-yl)-2-methyl-3-propyl-1,4-diaza-1,3-butadiene]nickel dichloride),
1,4-bis(azacyclohept-1-yl)-2-methyl-3-propyl-1,4-diaza-1,3-butadiene]nickel dichloride (1,4-bis(homopiperidin-1-yl)-2-methyl-3-propyl-1,4-diaza-1,3-butadiene]nickel dichloride),
1,4-bis(azacyclooct-1-yl)-2-methyl-3-propyl-1,4-diaza-1,3-butadiene]nickel dichloride,
1,4-bis(azacyclonon-1-yl)-2-methyl-3-propyl-1,4-diaza-1,3-butadiene]nickel dichloride,
1,4-bis(azacyclodec-1-yl)-2-methyl-3-propyl-1,4-diaza-1,3-butadiene]nickel dichloride,
1,4-bis(azacycloundec-1-yl)-2-methyl-3-propyl-1,4-diaza-1,3-butadiene]nickel dichloride,
1,4-bis(azacyclododec-1-yl)-2-methyl-3-propyl-1,4-diaza-1,3-butadiene]nickel dichloride,
1,4-bis(azacyclotetradec-1-yl)-2-methyl-3-propyl-1,4-diaza-1,3-butadiene]nickel dichloride,
1,4-bis(azacyclohexadec-1-yl)-2-methyl-3-propyl-1,4-diaza-1,3-butadiene]nickel dichloride,
1,4-bis(azacyclooctadec-1-yl)-2-methyl-3-propyl-1,4-diaza-1,3-butadiene]nickel dichloride,
1,4-bis(imidazolidin-1-yl)-2-methyl-3-propyl-1,4-diaza-1,3-butadiene]nickel dichloride,
1,4-bis(piperazin-1-yl)-2-methyl-3-propyl-1,4-diaza-1,3-butadiene]nickel dichloride,
1,4-bis(pyrazolidin-1-yl)-2-methyl-3-propyl-1,4-diaza-1,3-butadiene]nickel dichloride,
1,4-bis(azacyclopent-1-yl)-1,4-diaza-1,3-butadiene]nickel dibromide (1,4-bis(pyrrolidin-1-yl)-1,4-diaza-1,3-butadiene]nickel dibromide),
1,4-bis(azacyclohex-1-yl)-1,4-diaza-1,3-butadiene]nickel dibromide (1,4-bis(piperidin-1-yl)-1,4-diaza-1,3-butadiene]nickel dibromide),
1,4-bis(azacyclohept-1-yl)-1,4-diaza-1,3-butadiene]nickel dibromide (1,4-bis(homopiperidin-1-yl)-1,4-diaza-1,3-butadiene]nickel dibromide),
1,4-bis(azacyclooct-1-yl)-1,4-diaza-1,3-butadiene]nickel dibromide,
1,4-bis(azacyclonon-1-yl)-1,4-diaza-1,3-butadiene]nickel dibromide,
1,4-bis(azacyclodec-1-yl)-1,4-diaza-1,3-butadiene]nickel dibromide,
1,4-bis(azacycloundec-1-yl)-1,4-diaza-1,3-butadiene]nickel dibromide, 1,4-bis(azacyclododec-1-yl)-1,4-diaza-1,3-butadiene]nickel dibromide,
1,4-bis(azacyclotetradec-1-yl)-1,4-diaza-1,3-butadiene] nickel dibromide,
1,4-bis(azacyclohexadec-1-yl)-1,4-diaza-1,3-butadiene] nickel dibromide,
1,4-bis(azacyclooctadec-1-yl)-1,4-diaza-1,3-butadiene] nickel dibromide,
1,4-bis(imidazolidin-1-yl)-1,4-diaza-1,3-butadiene]nickel dibromide,
1,4-bis(piperazin-1-yl)-1,4-diaza-1,3-butadiene]nickel dibromide,
1,4-bis(pyrazolidin-1-yl)-1,4-diaza-1,3-butadiene]nickel dibromide,
1,4-bis(azacyclopent-1-yl)-2,3-dimethyl-1,4-diaza-1,3-butadiene]nickel dibromide (1,4-bis(pyrrolidin-1-yl)-2,3-dimethyl-1,4-diaza-1,3-butadiene]nickel dibromide),
1,4-bis(azacyclohex-1-yl)-2,3-dimethyl-1,4-diaza-1,3-butadiene]nickel dibromide (1,4-bis(piperidin-1-yl)-2,3-dimethyl-1,4-diaza-1,3-butadienelnickel dibromide),
1,4-bis(azacyclohept-1-yl)-2,3-dimethyl-1,4-diaza-1,3-butadiene]nickel dibromide (1,4-bis(homopiperidin-1-yl)-2,3-dimethyl-1,4-diaza-1,3-butadiene]nickel dibromide),
1,4-bis(azacyclooct-1-yl)-2,3-dimethyl-1,4-diaza-1,3-butadiene]nickel dibromide,
1,4-bis(azacyclonon-1-yl)-2,3-dimethyl-1,4-diaza-1,3-butadiene]nickel dibromide,
1,4-bis(azacyclodec-1-yl)-2,3-dimethyl-1,4-diaza-1,3-butadiene]nickel dibromide,
1,4-bis(azacycloundec-1-yl)-2,3-dimethyl-1,4-diaza-1,3-butadiene]nickel dibromide,
1,4-bis(azacyclododec-1-yl)-2,3-dimethyl-1,4-diaza-1,3-butadiene]nickel dibromide,
1,4-bis(azacyclotetradec-1-yl)-2,3-dimethyl-1,4-diaza-1,3-butadiene]nickel dibromide,
1,4-bis(azacyclohexadec-1-yl)-2,3-dimethyl-1,4-diaza-1,3-butadiene]nickel dibromide,
1,4-bis(azacyclooctadec-1-yl)-2,3-dimethyl-1,4-diaza-1,3-butadiene]nickel dibromide,
1,4-bis(imidazolidin-1-yl)-2,3-dimethyl-1,4-diaza-1,3-butadiene]nickel dibromide,
1,4-bis(piperazin-1-yl)-2,3-dimethyl-1,4-diaza-1,3-butadiene]nickel dibromide,
1,4-bis(pyrazolidin-1-yl)-2,3-dimethyl-1,4-diaza-1,3-butadiene]nickel dibromide,
1,4-bis(azacyclopent-1-yl)-1,4-diaza-1,3-butadiene]palladium dichloride (1,4-bis(pyrrolidin-1-yl)-1,4-diaza-1,3-butadiene]palladium dichloride),
1,4-bis(azacyclohex-1-yl)-1,4-diaza-1,3-butadiene]palladium dichloride (1,4-bis(piperidin-1-yl)-1,4-diaza-1,3-butadiene]palladium dichloride),
1,4-bis(azacyclohept-1-yl)-1,4-diaza-1,3-butadiene]palladium dichloride (1,4-bis(homopiperidin-1-yl)-1,4-diaza-1,3-butadiene]palladium dichloride),
1,4-bis(azacyclooct-1-yl)-1,4-diaza-1,3-butadiene]palladium dichloride,
1,4-bis(azacyclonon-1-yl)-1,4-diaza-1,3-butadiene]palladium dichloride,
1,4-bis(azacyclodec-1-yl)-1,4-diaza-1,3-butadiene]palladium dichloride,
1,4-bis(azacycloundec-1-yl)-1,4-diaza-1,3-butadiene]palladium dichloride,
1,4-bis(azacyclododec-1-yl)-1,4-diaza-1,3-butadiene]palladium dichloride,
1,4-bis(azacyclotetradec-1-yl)-1,4-diaza-1,3-butadiene]palladium dichloride,
1,4-bis(azacyclohexadec-1-yl)-1,4-diaza-1,3-butadiene]palladium dichloride,
1,4-bis(azacyclooctadec-1-yl)-1,4-diaza-1,3-butadiene]palladium dichloride,
1,4-bis(imidazolidin-1-yl)-1,4-diaza-1,3-butadiene]palladium dichloride,
1,4-bis(piperazin-1-yl)-1,4-diaza-1,3-butadiene]palladium dichloride,
1,4-bis(pyrazolidin-1-yl)-1,4-diaza-1,3-butadiene]palladium dichloride,
1,4-bis(azacyclopent-1-yl)-2,3-dimethyl-1,4-diaza-1,3-butadiene]palladium dichloride (1,4-bis(pyrrolidin-1-yl)-2,3-dimethyl-1,4-diaza-1,3-butadiene]palladium dichloride),
1,4-bis(azacyclohex-1-yl)-2,3-dimethyl-1,4-diaza-1,3-butadiene]palladium dichloride (1,4-bis(piperidin-1-yl)-2,3-dimethyl-1,4-diaza-1,3-butadiene]palladium dichloride),
1,4-bis(azacyclohept-1-yl)-2,3-dimethyl-1,4-diaza-1,3-butadiene]palladium dichloride (1,4-bis(homopiperidin-1-yl)-2,3-dimethyl-1,4-diaza-1,3-butadiene]palladium dichloride),
1,4-bis(azacyclooct-1-yl)-2,3-dimethyl-1,4-diaza-1,3-butadiene]palladium dichloride,
1,4-bis(azacyclonon-1-yl)-2,3-dimethyl-1,4-diaza-1,3-butadiene]palladium dichloride,
1,4-bis(azacyclodec-1-yl)-2,3-dimethyl-1,4-diaza-1,3-butadiene]palladium dichloride,
1,4-bis(azacycloundec-1-yl)-2,3-dimethyl-1,4-diaza-1,3-butadiene]palladium dichloride,
1,4-bis(azacyclododec-1-yl)-2,3-dimethyl-1,4-diaza-1,3-butadiene]palladium dichloride,
1,4-bis(azacyclotetradec-1-yl)-2,3-dimethyl-1,4-diaza-1,3-butadiene]palladium dichloride,
1,4-bis(azacyclohexadec-1-yl)-2,3-dimethyl-1,4-diaza-1,3-butadiene]palladium dichloride,
1,4-bis(azacyclooctadec-1-yl)-2,3-dimethyl-1,4-diaza-1,3-butadiene]palladium dichloride,
1,4-bis(imidazolidin-1-yl)-2,3-dimethyl-1,4-diaza-1,3-butadiene]palladium dichloride,
1,4-bis(piperazin-1-yl)-2,3-dimethyl-1,4-diaza-1,3-butadiene]palladium dichloride, and
1,4-bis(pyrazolidin-1-yl)-2,3-dimethyl-1,4-diaza-1,3-butadiene]palladium dichloride.

Examples of compounds with non-symmetrical ligand structures containing saturated heteroalicyclic ring structures include:
1-(azacyclohex-1-yl)-4-(azacyclopent-1-yl)-1,4-diaza-1,3-butadiene]nickel dichloride,
1-(azacyclohept-1-yl)-4-(azacyclopent-1-yl)-1,4-diaza-1,3-butadiene]nickel dichloride,
1-(azacyclooct-1-yl)-4-(azacyclopent-1-yl)-1,4-diaza-1,3-butadiene]nickel dichloride,
1-(azacyclonon-1-yl)-4-(azacyclopent-1-yl)-1,4-diaza-1,3-butadiene]nickel dichloride,
1-(azacyclodec-1-yl)-4-(azacyclopent-1-yl)-1,4-diaza-1,3-butadiene]nickel dichloride,
1-bis(azacycloundec-1-yl)-4-(azacyclopent-1-yl)-1,4-diaza-1,3-butadiene]nickel dichloride,
1-(azacyclododec-1-yl)-4-(azacyclopent-1-yl)-1,4-diaza-1,3-butadiene]nickel dichloride,
1-(azacyclotetradec-1-yl)-4-(azacyclopent-1-yl)-1,4-diaza-1,3-butadiene]nickel dichloride,
1-(azacyclohexadec-1-yl)-4-(azacyclopent-1-yl)-1,4-diaza-1,3-butadiene]nickel dichloride,
1-(azacyclooctadec-1-yl)-4-(azacyclopent-1-yl)-1,4-diaza-1,3-butadiene]nickel dichloride, 1-(indolin-1-yl)-4-(azacyclopent-1-yl)-1,4-diaza-1,3-butadiene]nickel dichloride,
1-(isoindolin-2-yl)-4-(azacyclopent-1-yl)-1,4-diaza-1,3-butadiene]nickel dichloride,
1-(piperazin-1-yl)-4-(azacyclopent-1-yl)-1,4-diaza-1,3-butadiene]nickel dichloride,
1-(pyrazolidin-1-yl)-4-(azacyclopent-1-yl)-1,4-diaza-1,3-butadiene]nickel dichloride,
1-(azacyclohept-1-yl)-4-(azacyclohex-1-yl)-1,4-diaza-1,3-butadiene]nickel dichloride,
1-(azacyclooct-1-yl)-4-(azacyclohex-1-yl)-1,4-diaza-1,3-butadiene]nickel dichloride,
1-(azacyclonon-1-yl)-4-(azacyclohex-1-yl)-1,4-diaza-1,3-butadiene]nickel dichloride,
1-(azacyclodec-1-yl)-4-(azacyclohex-1-yl)-1,4-diaza-1,3-butadiene]nickel dichloride,
1-(azacycloundec-1-yl)-4-(azacyclohex-1-yl)-1,4-diaza-1,3-butadiene]nickel dichloride,
1-(azacyclododec-1-yl)-4-(azacyclohex-1-yl)-1,4-diaza-1,3-butadiene]nickel dichloride,
1-(azacyclotetradec-1-yl)-4-(azacyclohex-1-yl)-1,4-diaza-1,3-butadiene]nickel dichloride,
1-(azacyclohexadec-1-yl)-4-(azacyclohex-1-yl)-1,4-diaza-1,3-butadiene]nickel dichloride,
1-(azacyclooctadec-1-yl)-4-(azacyclohex-1-yl)-1,4-diaza-1,3-butadiene]nickel dichloride,
1-(indolin-1-yl)-4-(azacyclohex-1-yl)-1,4-diaza-1,3-butadiene]nickel dichloride,
1-(isoindolin-2-yl)-4-(azacyclohex-1-yl)-1,4-diaza-1,3-butadiene]nickel dichloride,
1-(piperazin-1-yl)-4-(azacyclohex-1-yl)-1,4-diaza-1,3-butadiene]nickel dichloride,
1-(pyrazolidin-1-yl)-4-(azacyclohex-1-yl)-1,4-diaza-1,3-butadiene]nickel dichloride,
1-(azacyclooct-1-yl)-4-(azacyclohept-1-yl)-1,4-diaza-1,3-butadiene]nickel dichloride,
1-(azacyclonon-1-yl)-4-(azacyclohept-1-yl)-1,4-diaza-1,3-butadiene]nickel dichloride,
1-(azacyclodec-1-yl)-4-(azacyclohept-1-yl)—1,4-diaza-1,3-butadiene]nickel dichloride,
1-(azacycloundec-1-yl)-4-(azacyclohept-1-yl)-1,4-diaza-1,3-butadiene]nickel dichloride,
1-(azacyclododec-1-yl)-4-(azacyclohept-1-yl)-1,4-diaza-1,3-butadiene]nickel dichloride,
1-(azacyclotetradec-1-yl)-4-(azacyclohept-1-yl)-1,4-diaza-1,3-butadiene]nickel dichloride,
1-(azacyclohexadec-1-yl)-4-(azacyclohept-1-yl)-1,4-diaza-1,3-butadiene]nickel dichloride,
1-(azacyclooctadec-1-yl)-4-(azacyclohept-1-yl)-1,4-diaza-1,3-butadiene]nickel dichloride,
1-(indolin-1-yl)-4-(azacyclohept-1-yl)-1,4-diaza-1,3-butadiene]nickel dichloride,
1-(isoindolin-2-yl)-4-(azacyclohept-1-yl)-1,4-diaza-1,3-butadiene]nickel dichloride,
1-(piperazin-1-yl)-4-(azacyclohept-1-yl)-1,4-diaza-1,3-butadiene]nickel dichloride,
1-(pyrazolidin-1-yl)-4-(azacyclohept-1-yl)-1,4-diaza-1,3-butadiene]nickel dichloride,
1-(azacyclonon-1-yl)-4-(azacyclooct-1-yl)-1,4-diaza-1,3-butadiene]nickel dichloride,
1-(azacyclodec-1-yl)-4-(azacyclooct-1-yl)-1,4-diaza-1,3-butadiene]nickel dichloride,
1-(azacycloundec-1-yl)-4-(azacyclooct-1-yl)-1,4-diaza-1,3-butadiene]nickel dichloride,
1-(azacyclododec-1-yl)-4-(azacyclooct-1-yl)-1,4-diaza-1,3-butadiene]nickel dichloride,
1-(azacyclotetradec-1-yl)-4-(azacyclooct-1-yl)-1,4-diaza-1,3-butadiene]nickel dichloride,
1-(azacyclohexadec-1-yl)-4-(azacyclooct-1-yl)-1,4-diaza-1,3-butadiene]nickel dichloride,
1-(azacyclooctadec-1-yl)-4-(azacyclooct-1-yl)-1,4-diaza-1,3-butadiene]nickel dichloride,
1-(indolin-1-yl)-4-(azacyclooct-1-yl)-1,4-diaza-1,3-butadiene]nickel dichloride,
1-(isoindolin-2-yl)-4-(azacyclooct-1-yl)-1,4-diaza-1,3-butadiene]nickel dichloride,
1-(piperazin-1-yl)-4-(azacyclooct-1-yl)-1,4-diaza-1,3-butadiene]nickel dichloride,
1-(pyrazolidin-1-yl)-4-(azacyclooct-1-yl)-1,4-diaza-1,3-butadiene]nickel dichloride,
1-(azacyclodec-1-yl)-4-(azacyclonon-1-yl)-1,4-diaza-1,3-butadiene]nickel dichloride,
1-(azacycloundec-1-yl)-4-(azacyclonon-1-yl)-1,4-diaza-1,3-butadiene]nickel dichloride,
1-(azacyclododec-1-yl)-4-(azacyclonon-1-yl)-1,4-diaza-1,3-butadiene]nickel dichloride,
1-(azacyclotetradec-1-yl)-4-(azacyclonon-1-yl)-1,4-diaza-1,3-butadiene]nickel dichloride,
1-(azacyclohexadec-1-yl)-4-(azacyclonon-1-yl)-1,4-diaza-1,3-butadiene]nickel dichloride,
1-(azacyclooctadec-1-yl)-4-(azacyclonon-1-yl)-1,4-diaza-1,3-butadiene]nickel dichloride,
1-(indolin-1-yl)-4-(azacyclonon-1-yl)-1,4-diaza-1,3-butadiene]nickel dichloride,
1-(isoindolin-2-yl)-4-(azacyclonon-1-yl)-1,4-diaza-1,3-butadiene]nickel dichloride,
1-(piperazin-1-yl)-4-(azacyclonon-1-yl)-1,4-diaza-1,3-butadiene]nickel dichloride,
1-(pyrazolidin-1-yl)-4-(azacyclonon-1-yl)-1,4-diaza-1,3-butadiene]nickel dichloride,
1-(azacycloundec-1-yl)-4-(azacyclodec-1-yl)-1,4-diaza-1,3-butadiene]nickel dichloride,
1-(azacyclododec-1-yl)-4-(azacyclodec-1-yl)-1,4-diaza-1,3-butadiene]nickel dichloride,
1-(azacyclotetradec-1-yl)-4-(azacyclodec-1-yl)-1,4-diaza-1,3-butadiene]nickel dichloride,
1-(azacyclohexadec-1-yl)-4-(azacyclodec-1-yl)-1,4-diaza-1,3-butadiene]nickel dichloride,
1-(azacyclooctadec-1-yl)-4-(azacyclodec-1-yl)-1,4-diaza-1,3-butadiene]nickel dichloride,
1-(indolin-1-yl)-4-(azacyclodec-1-yl)-1,4-diaza-1,3-butadiene]nickel dichloride,
1-(isoindolin-2-yl)-4-(azacyclodec-1-yl)-1,4-diaza-1,3-butadiene]nickel dichloride,
1-(piperazin-1-yl)-4-(azacyclodec-1-yl)-1,4-diaza-1,3-butadiene]nickel dichloride,
1-(pyrazolidin-1-yl)-4-(azacyclodec-1-yl)-1,4-diaza-1,3-butadiene]nickel dichloride,
1-(azacyclododec-1-yl)-4-(azacycloundec-1-yl)-1,4-diaza-1,3-butadiene]nickel dichloride,
1-(azacyclotetradec-1-yl)-4-(azacycloundec-1-yl)-1,4-diaza-1,3-butadiene]nickel dichloride,
1-(azacyclohexadec-1-yl)-4-(azacycloundec-1-yl)-1,4-diaza-1,3-butadiene]nickel dichloride,
1-(azacyclooctadec-1-yl)-4-(azacycloundec-1-yl)-1,4-diaza-1,3-butadiene]nickel dichloride,
1-(indolin-1-yl)-4-(azacycloundec-1-yl)-1,4-diaza-1,3-butadiene]nickel dichloride,
1-(isoindolin-2-yl)-4-(azacycloundec-1-yl)-1,4-diaza-1,3-butadiene]nickel dichloride,
1-(piperazin-1-yl)-4-(azacycloundec-1-yl)-1,4-diaza-1,3-butadiene]nickel dichloride, 1-(pyrazolidin-1-yl)-4-(azacycloundec-1-yl)-1,4-diaza-1,3-butadiene]nickel dichloride, 1-(azacyclotetradec-1-yl)-4-(azacyclododec-1-yl)-1,4-diaza-1,3-butadiene]nickel dichloride, 1-(azacyclohexadec-1-yl)-4-(azacyclododec-1-yl)-1,4-diaza-1,3-butadiene]nickel dichloride, 1-(azacyclooctadec-1-yl)-4-(azacyclododec-1-yl)-1,4-diaza-1,3-butadiene]nickel dichloride, 1-(indolin-1-yl)-4-(azacyclododec-1-yl)-1,4-diaza-1,3-butadiene]nickel dichloride, 1-(isoindolin-2-yl)-4-(azacyclododec-1-yl)-1,4-diaza-1,3-butadiene]nickel dichloride, 1-(piperazin-1-yl)-4-(azacyclododec-1-yl)-1,4-diaza-1,3-butadiene]nickel dichloride, 1-(pyrazolidin-1-yl)-4-(azacyclododec-1-yl)-1,4-diaza-1,3-butadiene]nickel dichloride, 1-(azacyclohexadec-1-yl)-4-(azacyclotetradec-1-yl)-1,4-diaza-1,3-butadiene]nickel dichloride, 1-(azacyclooctadec-1-yl)-4-(azacyclotetradec-1-yl)-1,4-diaza-1,3-butadiene]nickel dichloride, 1-(indolin-1-yl)-4-(azacyclotetradec-1-yl)-1,4-diaza-1,3-butadiene]nickel dichloride, 1-(isoindolin-2-yl)-4-(azacyclotetradec-1-yl)-1,4-diaza-1,3-butadiene]nickel dichloride, 1-(piperazin-1-yl)-4-(azacyclotetradec-1-yl)-1,4-diaza-1,3-butadiene]nickel dichloride, 1-(pyrazolidin-1-yl)-4-(azacyclotetradec-1-yl)-1,4-diaza-1,3-butadiene]nickel dichloride, 1-(azacyclooctadec-1-yl)-4(azacyclohexadec-1-yl)-1,4-diaza-1,3-butadiene]nickel dichloride, 1-(indolin-1-yl)-4-(azacyclohexadec-1-yl)-1,4-diaza-1,3-butadiene]nickel dichloride, 1-(isoindolin-2-yl)-4-(azacyclohexadec-1-yl)-1,4-diaza-1,3-butadiene]nickel dichloride, 1-(piperazin-1-yl)-4-(azacyclohexadec-1-yl)-1,4-diaza-1,3-butadiene]nickel dichloride, 1-(pyrazolidin-1-yl)-4-(azacyclohexadec-1-yl)-1,4-diaza-1,3-butadiene]nickel dichloride, 1-(indolin-1-yl)-4-1-(azacyclooctadec-1-yl)-1,4-diaza-1,3-butadiene]nickel dichloride, 1-(isoindolin-2-yl)-4-1-(azacyclooctadec-1-yl)-1,4-diaza-1,3-butadiene]nickel dichloride, 1-(piperazin-1-yl)-4-1-(azacyclooctadec-1-yl)-1,4-diaza-1,3-butadiene]nickel dichloride, 1-(pyrazolidin-1-yl)-4-1-(azacyclooctadec-1-yl)-1,4-diaza-1,3-butadiene]nickel dichloride, 1-(isoindolin-2-yl)-4-1-(indolin-1-yl)-1,4-diaza-1,3-butadiene]nickel dichloride, 1-(piperazin-1-yl)-4-1-(indolin-1-yl)-1,4-diaza-1,3-butadiene]nickel dichloride, 1-(pyrazolidin-1-yl)-4-1-(indolin-1-yl)-1,4-diaza-1,3-butadiene]nickel dichloride, 1-(piperazin-1-yl)-4-(isoindolin-2-yl)-1,4-diaza-1,3-butadiene]nickel dichloride, 1-(pyrazolidin-1-yl)-4-(isoindolin-2-yl)-1,4-diaza-1,3-butadiene]nickel dichloride, and 1-(pyrazolidin-1-yl)-4—(piperazin-1-yl)—1,4-diaza-1,3-butadiene]nickel dichloride.

Examples of compounds with symmetrical ligand structures containing substituted heteroalicyclic ring structures include:

1,4-bis(3-methylazacyclopent-1-yl)-1,4-diaza-1,3-butadiene]nickel dichloride (1,4-bis(3-methyl-pyrrolidin-1-yl)-1,4-diaza-1,3-butadiene]nickel dichloride), 1,4-bis(3,4-dimethylazacyclopent-1-yl)-1,4-diaza-1,3-butadiene]nickel dichloride (1,4-bis(3,4-dimethyl-pyrrolidin-1-yl)-1,4-diaza-1,3-butadiene]nickel dichloride), 1,4-bis(3,3-dimethylazacyclopent-1-yl)-1,4-diaza-1,3-butadiene]nickel dichloride (1,4-bis(3,3-dimethyl-pyrrolidin-1-yl)-1,4-diaza-1,3-butadiene]nickel dichloride), 1,4-bis(3,3,4-trimethylazacyclopent-1-yl)-1,4-diaza-1,3-butadiene]nickel dichloride (1,4-bis(3,3,4-trimethyl-pyrrolidin-1-yl)-1,4-diaza-1,3-butadiene]nickel dichloride), 1,4-bis(3,3,4,4-tetramethylazacyclopent1-1yl)-1,4-diaza-1,3-butadiene]nickel dichloride (1,4-bis(3,3,4,4-tetramethyl-pyrrolidin-1-yl)-1,4-diaza-1,3-butadiene]nickel dichloride), 1,4-bis(3-methylazacyclohex-1-yl)-1,4-diaza-1,3-butadiene]nickel dichloride (1,4-bis(3-methyl-piperidin-1-yl)-1,4-diaza-1,3-butadiene]nickel dichloride), 1,4-bis(4-methylazacyclohex-1-yl)-1,4-diaza-1,3-butadiene]nickel dichloride (1,4-bis(4-methyl-piperidin-1-yl)-1,4-diaza-1,3-butadiene]nickel dichloride), 1,4-bis(3,3-dimethylazacyclohex-1-yl)-1,4-diaza-1,3-butadiene]nickel dichloride (1,4-bis(3,3-dimethylpiperidin-1-yl)-1,4-diaza-1,3-butadiene]nickel dichloride), 1,4-bis(4,4-dimethylazacyclohex-1-yl)-1,4-diaza-1,3-butadiene]nickel dichloride (1,4-bis(4,4-dimethylpiperidin-1-yl)-1,4-diaza-1,3-butadiene]nickel dichloride), 1,4-bis(3,4-dimethylazacyclohex-1-yl)-1,4-diaza-1,3-butadiene]nickel dichloride (1,4-bis(3,4-dimethylpiperidin-1-yl)-1,4-diaza-1,3-butadiene]nickel dichloride), 1,4-bis(3,5-dimethylazacyclohex-1-yl)-1,4-diaza-1,3-butadiene]nickel dichloride (1,4-bis(3,5-dimethylpiperidin-1-yl)-1,4-diaza-1,3-butadiene]nickel dichloride), 1,4-bis(3,4,5-trimethylazacyclohex-1-yl)-1,4-diaza-1,3-butadiene]nickel dichloride (1,4-bis(3,4,5-trimethylpiperidin-1-yl)-1,4-diaza-1,3-butadiene]nickel dichloride), 1,4-bis(3,3,4-trimethylazacyclohex-1-yl)-1,4-diaza-1,3-butadiene]nickel dichloride (1,4-bis(3,3,4-trimethylpiperidin-1-yl)-1,4-diaza-1,3-butadiene]nickel dichloride), 1,4-bis(3,4,4-trimethylazacyclohex-1-yl)-1,4-diaza-1,3-butadiene]nickel dichloride (1,4-bis(3,4,4-trimethylpiperidin-1-yl)-1,4-diaza-1,3-butadiene]nickel dichloride), 1,4-bis(3,3,4,4-tetramethylazacyclohex-1-yl)-1,4-diaza-1,3-butadiene]nickel dichloride (1,4-bis(3,3,4,4-tetramethylpiperidin-1-yl)-1,4-diaza-1,3-butadiene]nickel dichloride), 1,4-bis(3,3,5,5-tetramethylazacyclohex-1-yl)-1,4-diaza-1,3-butadiene]nickel dichloride (1,4-bis(3,3,5,5-tetramethylpiperidin-1-yl)-1,4-diaza-1,3-butadiene]nickel dichloride), 1,4-bis(3,3,4,5-tetramethylazacyclohex-1-yl)-1,4-diaza-1,3-butadiene]nickel dichloride (1,4-bis(3,3,4,5-tetramethylpiperidin-1-yl)-1,4-diaza-1,3-butadiene]nickel dichloride), 1,4-bis(3,4,4,5-tetramethylazacyclohex-1-yl)-1,4-diaza-1,3-butadiene]nickel dichloride (1,4-bis(3,4,4,5-tetramethylpiperidin-1-yl)-1,4-diaza-1,3-butadiene]nickel dichloride), 1,4-bis(3,3,4,4,5-pentamethylazacyclohex-1-yl)-1,4-diaza-1,3-butadiene]nickel dichloride (1,4-bis(3,3,4,4,5-pentamethylpiperidin-1-yl)-1,4-diaza-1,3-butadiene]nickel dichloride), 1,4-bis(3,3,4,5,5-pentamethylazacyclohex-1-yl)-1,4-diaza-1,3-butadiene]nickel dichloride (1,4-bis(3,3,4,5,5-pentamethylpiperidin-1-yl)-1,4-diaza-1,3-butadiene]nickel dichloride), and 1,4-bis(3,3,4,4,5,5-hexamethylazacyclohex-1-yl)-1,4-diaza-1,3-butadiene]nickel dichloride (1,4-bis(3,3,4,4,5,5-hexamethylpiperidin-1-yl)-1,4-diaza-1,3-butadiene]nickel dichloride).

Examples of compounds with symmetrical ligand structures containing partially unsaturated heteroalicyclic ring structures include:

1,4-bis(azacyclopent-3-en-1-yl)-1,4-diaza-1,3-butadiene] nickel dichloride,
1,4-bis(azacyclopent-2-en-1-yl)-1,4-diaza-1,3-butadiene] nickel dichloride,
1,4-bis(azacyclohex-2-en-1-yl)-1,4-diaza-1,3-butadiene] nickel dichloride,
1,4-bis(azacyclohex-3-en-1-yl)-1,4-diaza-1,3-butadiene] nickel dichloride,
1,4-bis(azacyclohex-2,4-dien-1-yl)-1,4-diaza-1,3-butadiene]nickel dichloride,
1,4-bis(azacyclohex-2,5-dien-1-yl)-1,4-diaza-1,3-butadiene]nickel dichloride,
1,4-bis(azacyclohept-2-en-1-yl)-1,4-diaza-1,3-butadiene] nickel dichloride,
1,4-bis(azacyclohept-3-en-1-yl)-1,4-diaza-1,3-butadiene] nickel dichloride,
1,4-bis(azacyclohept-4-en-1-yl)-1,4-diaza-1,3-butadiene] nickel dichloride,
1,4-bis(azacyclohept-2,4-dien-1-yl)-1,4-diaza-1,3-butadiene]nickel dichloride,
1,4-bis(azacyclohept-2,5-dien-1-yl)-1,4-diaza-1,3-butadiene]nickel dichloride,
1,4-bis(azacyclohept-2,6-dien-1-yl)-1,4-diaza-1,3-butadienelnickel dichloride,
1,4-bis(azacyclohept-3,5-dien-1-yl)-1,4-diaza-1,3-butadiene]nickel dichloride,
1,4-bis(azacyclooct-2-en-1-yl)-1,4-diaza-1,3-butadiene] nickel dichloride,
1,4-bis(azacyclooct-3-en-1-yl)-1,4-diaza-1,3-butadiene] nickel dichloride,
1,4-bis(azacyclooct-4-en-1-yl)-1,4-diaza-1,3-butadiene] nickel dichloride,
1,4-bis(azacyclooct-2,4-dien-1-yl)-1,4-diaza-1,3-butadiene] nickel dichloride,
1,4-bis(azacyclooct-2,5-dien-1-yl)-1,4-diaza-1,3-butadiene] nickel dichloride,
1,4-bis(azacyclooct-2,6-dien-1-yl)-1,4-diaza-1,3-butadienelnickel dichloride,
1,4-bis(azacyclooct-2,7-dien-1-yl)-1,4-diaza-1,3-butadiene] nickel di chloride,
1,4-bis(azacyclooct-3,5-dien-1-yl)-1,4-diaza-1,3-butadiene] nickel dichloride,
1,4-bis(azacyclooct-3,6-dien-1-yl)-1,4-diaza-1,3-butadiene] nickel dichloride,
1,4-bis(azacyclooct-4,6-dien-1-yl)-1,4-diaza-1,3-butadiene] nickel dichloride,
1,4-bis(azacyclonon-2-en-1-yl)-1,4-diaza-1,3-butadiene] nickel dichloride,
1,4-bis(azacyclonon-3-en-1-yl)-1,4-diaza-1,3-butadiene] nickel dichloride,
1,4-bis(azacyclonon-4-en-1-yl)-1,4-diaza-1,3-butadiene] nickel dichloride,
1,4-bis(azacyclonon-5-en-1-yl)-1,4-diaza-1,3-butadiene] nickel dichloride,
1,4-bis(azacyclonon-2,4-dien-1-yl)-1,4-diaza-1,3-butadiene]nickel dichloride,
1,4-bis(azacyclonon-2,5-dien-1-yl)-1,4-diaza-1,3-butadiene]nickel dichloride,
1,4-bis(azacyclonon-2,6-dien-1-yl)-1,4-diaza-1,3-butadiene]nickel dichloride,
1,4-bis(azacyclonon-2,7-dien-1-yl)-1,4-diaza-1,3-butadiene]nickel dichloride,
1,4-bis(azacyclonon-2,8-dien-1-yl)-1,4-diaza-1,3-butadiene]nickel dichloride,
1,4-bis(azacyclonon-3,5-dien-1-yl)-1,4-diaza-1,3-butadiene]nickel dichloride,
1,4-bis(azacyclonon-3,6-dien-1-yl)-1,4-diaza-1,3-butadiene]nickel dichloride,
1,4-bis(azacyclonon-3,7-dien-1-yl)-1,4-diaza-1,3-butadiene]nickel dichloride,
1,4-bis(azacyclonon-4,6-dien-1-yl)-1,4-diaza-1,3-butadiene]nickel dichloride,
1,4-bis(azacyclodec-2-en-1-yl)-1,4-diaza-1,3-butadiene] nickel dichloride,
1,4-bis(azacyclodec-3-en-1-yl)-1,4-diaza-1,3-butadiene] nickel dichloride,
1,4-bis(azacyclodec-4-en-1-yl)-1,4-diaza-1,3-butadiene] nickel dichloride,
1,4-bis(azacyclodec-5-en-1-yl)-1,4-diaza-1,3-butadiene] nickel dichloride,
1,4-bis(azacyclodec-2,4-dien-1-yl)-1,4-diaza-1,3-butadiene]nickel dichloride,
1,4-bis(azacyclodec-2,5-dien-1-yl)-1,4-diaza-1,3-butadiene]nickel dichloride,
1,4-bis(azacyclodec-2,6-dien-1-yl)-1,4-diaza-1,3-butadiene]nickel dichloride,
1,4-bis(azacyclodec-2,7-dien-1-yl)-1,4-diaza-1,3-butadiene]nickel dichloride,
1,4-bis(azacyclodec-2,8-dien-1-yl)-1,4-diaza-1,3-butadiene]nickel dichloride,
1,4-bis(azacyclodec-2,9-dien-1-yl)-1,4-diaza-1,3-butadiene]nickel dichloride,
1,4-bis(azacyclodec-3,5-dien-1-yl)-1,4-diaza-1,3-butadiene]nickel dichloride,
1,4-bis(azacyclodec-3,6-dien-1-yl)-1,4-diaza-1,3-butadiene]nickel dichloride,
1,4-bis(azacyclodec-3,7-dien-1-yl)-1,4-diaza-1,3-butadiene]nickel dichloride,
1,4-bis(azacyclodec-3,8-dien-1-yl)-1,4-diaza-1,3-butadiene]nickel dichloride,
1,4-bis(azacyclodec-4,6-dien-1-yl)-1,4-diaza-1,3-butadiene]nickel dichloride,
1,4-bis(azacyclodec-4,7-dien-1-yl)-1,4-diaza-1,3-butadiene]nickel dichloride,
1,4-bis(azacycloundec-2-en-1-yl)-1,4-diaza-1,3-butadiene] nickel dichloride,
1,4-bis(azacycloundec-3-en-1-yl)-1,4-diaza-1,3-butadiene] nickel dichloride,
1,4-bis(azacycloundec-4-en-1-yl)-1,4-diaza-1,3-butadiene] nickel dichloride,
1,4-bis(azacycloundec-5-en-1-yl)-1,4-diaza-1,3-butadiene] nickel dichloride,
1,4-bis(azacycloundec-6-en-1-yl)-1,4-diaza-1,3-butadiene] nickel dichloride,
1,4-bis(azacyclododec-2-en-1-yl)-1,4-diaza-1,3-butadiene] nickel dichloride,
1,4-bis(azacyclododec-3-en-1-yl)-1,4-diaza-1,3-butadiene] nickel dichloride,
1,4-bis(azacyclododec-4-en-1-yl)-1,4-diaza-1,3-butadiene] nickel dichloride,
1,4-bis(azacyclododec-5-en-1-yl)-1,4-diaza-1,3-butadiene] nickel dichloride,
1,4-bis(azacyclododec-6-en-1-yl)-1,4-diaza-1,3-butadiene] nickel dichloride,
1,4-bis(azacyclotetradec-2-en-1-yl)-1,4-diaza-1,3-butadiene]nickel dichloride, 1,4-bis(azacyclotetradec-3-en-1-yl)-1,4-diaza-1,3-butadiene]nickel dichloride,
1,4-bis(azacyclotetradec-4-en-1-yl)-1,4-diaza-1,3-butadiene]nickel dichloride,
1,4-bis(azacyclotetradec-5-en-1-yl)-1,4-diaza-1,3-butadiene]nickel dichloride,
1,4-bis(azacyclotetradec-6-en-1-yl)-1,4-diaza-1,3-butadiene]nickel dichloride,
1,4-bis(azacyclotetradec-7-en-1-yl)-1,4-diaza-1,3-butadiene]nickel dichloride,
1,4-bis(azacyclohexadec-2-en-1-yl)-1,4-diaza-1,3-butadiene]nickel dichloride,
1,4-bis(azacyclohexadec-3-en-1-yl)-1,4-diaza-1,3-butadiene]nickel dichloride,
1,4-bis(azacyclohexadec-4-en-1-yl)-1,4-diaza-1,3-butadiene]nickel dichloride,
1,4-bis(azacyclohexadec-5-en-1-yl)-1,4-diaza-1,3-butadiene]nickel dichloride,
1,4-bis(azacyclohexadec-6-en-1-yl)-1,4-diaza-1,3-butadiene]nickel dichloride,
1,4-bis(azacyclohexadec-7-en-1-yl)-1,4-diaza-1,3-butadiene]nickel dichloride,
1,4-bis(azacyclohexadec-8-en-1-yl)-1,4-diaza-1,3-butadiene]nickel dichloride,
1,4-bis(azacyclooctadec-2-en-1-yl)-1,4-diaza-1,3-butadiene]nickel dichloride,
1,4-bis(azacyclooctadec-3-en-1-yl)-1,4-diaza-1,3-butadiene]nickel dichloride,
1,4-bis(azacyclooctadec-4-en-1-yl)-1,4-diaza-1,3-butadiene]nickel dichloride,
1,4-bis(azacyclooctadec-5-en-1-yl)-1,4-diaza-1,3-butadiene]nickel dichloride,
1,4-bis(azacyclooctadec-6-en-1-yl)-1,4-diaza-1,3-butadiene]nickel dichloride,
1,4-bis(azacyclooctadec-7-en-1-yl)-1,4-diaza-1,3-butadiene]nickel dichloride,
1,4-bis(azacyclooctadec-8-en-1-yl)-1,4-diaza-1,3-butadiene]nickel dichloride,
1,4-bis(azacyclooctadec-9-en-1-yl)-1,4-diaza-1,3-butadiene]nickel dichloride,
1,4-bis(indolin-1-yl)-1,4-diaza-1,3-butadiene]nickel dichloride, and
1,4-bis(isoindolin-2-yl)-1,4-diaza-1,3-butadiene]nickel dichloride.

Examples of compounds with symmetrical ligand structures containing partially unsaturated and substituted heteroalicyclic ring structures include:
1,4-bis(3-methylazacyclopent-3-en-1-yl)-1,4-diaza-1,3-butadiene]nickel dichloride (1,4-bis(3-methyl-2,5-dihydropyrrol-1-yl)-1,4-diaza-1,3-butadiene]nickel dichloride),
1,4-bis(3,4-dimethylazacyclopent-3-en-1-yl)-1,4-diaza-1,3-butadiene]nickel dichloride (1,4-bis(3,4-dimethyl-2,5-dihydropyrrol-1-yl)-1,4-diaza-1,3-butadiene]nickel dichloride),
1,4-bis(3-methylazacyclopent-2-en-1-yl)-1,4-diaza-1,3-butadiene]nickel dichloride (1,4-bis(3-methyl-4,5-dihydropyrrol-1-yl)-1,4-diaza-1,3-butadiene]nickel dichloride),
1,4-bis(4-methylazacyclopent-2-en-1-yl)-1,4-diaza-1,3-butadiene]nickel dichloride (1,4-bis(4-methyl-4,5-dihydropyrrol-1-yl)-1,4-diaza-1,3-butadiene]nickel dichloride),
1,4-bis(3,4-dimethylazacyclopent-2-en-1-yl)-1,4-diaza-1,3-butadiene]nickel dichloride (1,4-bis(3,4-dimethyl-4,5-dihydropyrrol-1-yl)-1,4-diaza-1,3-butadiene]nickel dichloride),
1,4-bis(4,4-dimethylazacyclopent-2-en-1-yl)-1,4-diaza-1,3-butadiene]nickel dichloride (1,4-bis(4,4-dimethyl-4,5-dihydropyrrol-1-yl)-1,4-diaza-1,3-butadiene]nickel dichloride),
1,4-bis(3,4,4-trimethylazacyclopent-2-en-1-yl)-1,4-diaza-1,3-butadiene]nickel dichloride (1,4-bis(3,4,4-trimethyl-4,5-dihydropyrrol-1-yl)-1,4-diaza-1,3-butadiene]nickel dichloride),
1,4-bis(3-methylazacyclohex-2-en-1-yl)-1,4-diaza-1,3-butadiene]nickel dichloride,
1,4-bis(4-methylazacyclohex-2-en-1-yl)-1,4-diaza-1,3-butadiene]nickel dichloride,
1,4-bis(5-methylazacyclohex-2-en-1-yl)-1,4-diaza-1,3-butadiene]nickel dichloride,
1,4-bis(4,4-dimethylazacyclohex-2-en-1-yl)-1,4-diaza-1,3-butadiene]nickel dichloride,
1,4-bis(5,5-dimethylazacyclohex-2-en-1-yl)-1,4-diaza-1,3-butadiene]nickel dichloride,
1,4-bis(3,4-dimethylazacyclohex-2-en-1-yl)-1,4-diaza-1,3-butadiene]nickel dichloride,
1,4-bis(3,5-dimethylazacyclohex-2-en-1-yl)-1,4-diaza-1,3-butadiene]nickel dichloride,
1,4-bis(4,5-dimethylazacyclohex-2-en-1-yl)-1,4-diaza-1,3-butadiene]nickel dichloride,
1,4-bis(3,4,5-trimethylazacyclohex-2-en-1-yl)-1,4-diaza-1,3-butadiene]nickel dichloride,
1,4-bis(3,4,4-trimethylazacyclohex-2-en-1-yl)-1,4-diaza-1,3-butadiene]nickel dichloride,
1,4-bis(3,5,5-trimethylazacyclohex-2-en-1-yl)-1,4-diaza-1,3-butadiene]nickel dichloride,
1,4-bis(3,4,4,5-tetramethylazacyclohex-2-en-1-yl)-1,4-diaza-1,3-butadiene]nickel dichloride,
1,4-bis(3,4,5,5-tetramethylazacyclohex-2-en-1-yl)-1,4-diaza-1,3-butadiene]nickel dichloride,
1,4-bis(3-methylazacyclohex-3-en-1-yl)-1,4-diaza-1,3-butadiene]nickel dichloride,
1,4-bis(4-methylazacyclohex-3-en-1-yl)-1,4-diaza-1,3-butadiene]nickel dichloride,
1,4-bis(5-methylazacyclohex-3-en-1-yl)-1,4-diaza-1,3-butadiene]nickel dichloride,
1,4-bis(3,4-dimethylazacyclohex-3-en-1-yl)-1,4-diaza-1,3-butadiene]nickel dichloride,
1,4-bis(3,5-dimethylazacyclohex-3-en-1-yl)-1,4-diaza-1,3-butadiene]nickel dichloride,
1,4-bis(4,5-dimethylazacyclohex-3-en-1-yl)-1,4-diaza-1,3-butadiene]nickel dichloride, and
1,4-bis(3,4,5-trimethylazacyclohex-3-en-1-yl)-1,4-diaza-1,3-butadiene]nickel dichloride.

Examples of compounds with symmetrical ligand structures not containing heteroalicyclic ring structures include:
1,4-bis(diethylamino)-1,4-diaza-1,3-butadiene]nickel dichloride,
1,4-bis(dipropylamino)-1,4-diaza-1,3-butadiene]nickel dichloride,
1,4-bis(dibutylamino)-1,4-diaza-1,3-butadiene]nickel dichloride,
1,4-bis(dipentylamino)-1,4-diaza-1,3-butadiene]nickel dichloride,
1,4-bis(dihexylamino)-1,4-diaza-1,3-butadiene]nickel dichloride,
1,4-bis(diheptylamino)-1,4-diaza-1,3-butadiene]nickel dichloride,
1,4-bis(dioctylamino)-1,4-diaza-1,3-butadiene]nickel dichloride,
1,4-bis(dinonylamino)-1,4-diaza-1,3-butadiene]nickel dichloride, 1,4-bis(didecylamino)-1,4-diaza-1,3-butadiene]nickel dichloride,
1,4-bis(diundecylamino)-1,4-diaza-1,3-butadiene]nickel dichloride,
1,4-bis(didodecylamino)-1,4-diaza-1,3-butadiene]nickel dichloride,
1,4-bis(dicyclopentylamino)-1,4-diaza-1,3-butadiene]nickel dichloride,
1,4-bis(dicyclohexylamino)-1,4-diaza-1,3-butadiene]nickel dichloride,
1,4-bis(dicyclohepylamino)-1,4-diaza-1,3-butadiene]nickel dichloride,
1,4-bis(dicyclooctylamino)-1,4-diaza-1,3-butadiene]nickel dichloride,
1,4-bis(dicyclononylamino)-1,4-diaza-1,3-butadiene]nickel dichloride,
1,4-bis(dicyclodecylamino)-1,4-diaza-1,3-butadiene]nickel dichloride,
1,4-bis(dicycloundecylamino)-1,4-diaza-1,3-butadiene] nickel dichloride,
1,4-bis(dicyclododecylamino)-1,4-diaza-1,3-butadiene] nickel dichloride,
1,4-bis(ethylpropylamino)-1,4-diaza-1,3-butadiene]nickel dichloride,
1,4-bis(ethylbutylamino)-1,4-diaza-1,3-butadiene]nickel dichloride,
1,4-bis(ethylpentylamino)-1,4-diaza-1,3-butadiene]nickel dichloride,
1,4-bis(ethylhexylamino)-1,4-diaza-1,3-butadiene]nickel dichloride,
1,4-bis(ethylheptylamino)-1,4-diaza-1,3-butadiene]nickel dichloride,
1,4-bis(ethyloctylamino)-1,4-diaza-1,3-butadienelnickel dichloride,
1,4-bis(ethylnonylamino)-1,4-diaza-1,3-butadiene]nickel dichloride,
1,4-bis(ethyldecylamino)-1,4-diaza-1,3-butadiene]nickel dichloride,
1,4-bis(ethylundecylamino)-1,4-diaza-1,3-butadiene]nickel dichloride,
1,4-bis(ethyldodecylamino)-1,4-diaza-1,3-butadiene]nickel dichloride,
1,4-bis(ethylcyclopentylamino)-1,4-diaza-1,3-butadiene] nickel dichloride,
1,4-bis(ethylcyclohexylamino)-1,4-diaza-1,3-butadiene] nickel dichloride,
1,4-bis(ethylcycloheptylamino)-1,4-diaza-1,3-butadiene] nickel dichloride,
1,4-bis(ethylcyclooctylamino)-1,4-diaza-1,3-butadiene] nickel dichloride,
1,4-bis(ethylcyclononylamino)-1,4-diaza-1,3-butadiene] nickel dichloride,
1,4-bis(ethylcyclodecylamino)-1,4-diaza-1,3-butadiene] nickel dichloride,
1,4-bis(ethylcycloundecylamino)-1,4-diaza-1,3-butadiene] nickel dichloride,
1,4-bis(ethylcyclododecylamino)-1,4-diaza-1,3-butadienelnickel dichloride,
1,4-bis(propylbutylamino)-1,4-diaza-1,3-butadiene]nickel dichloride,
1,4-bis(propylpentylamino)-1,4-diaza-1,3-butadiene]nickel dichloride,
1,4-bis(propylhexylamino)-1,4-diaza-1,3-butadiene]nickel dichloride,
1,4-bis(propylheptylamino)-1,4-diaza-1,3-butadiene]nickel dichloride,
1,4-bis(propyloctylamino)-1,4-diaza-1,3-butadiene]nickel dichloride,
1,4-bis(propylnonylamino)-1,4-diaza-1,3-butadiene]nickel dichloride,
1,4-bis(propyldecylamino)-1,4-diaza-1,3-butadiene]nickel dichloride,
1,4-bis(propylundecylamino)-1,4-diaza-1,3-butadiene] nickel dichloride,
1,4-bis(propyldodecylamino)-1,4-diaza-1,3-butadiene] nickel dichloride,
1,4-bis(propylcyclopentylamino)-1,4-diaza-1,3-butadiene] nickel dichloride,
1,4-bis(propylcyclohexylamino)-1,4-diaza-1,3-butadiene] nickel dichloride,
1,4-bis(propylcycloheptylamino)-1,4-diaza-1,3-butadiene] nickel dichloride,
1,4-bis(propylcyclooctylamino)-1,4-diaza-1,3-butadiene] nickel dichloride,
1,4-bis(propylcyclononylamino)-1,4-diaza-1,3-butadiene] nickel dichloride,
1,4-bis(propylcyclodecylamino)-1,4-diaza-1,3-butadiene] nickel dichloride,
1,4-bis(propylcycloundecylamino)-1,4-diaza-1,3-butadiene]nickel dichloride,
1,4-bis(propylcyclododecylamino)-1,4-diaza-1,3-butadiene]nickel dichloride,
1,4-bis(butylpentylamino)-1,4-diaza-1,3-butadiene]nickel dichloride,
1,4-bis(butylhexylamino)-1,4-diaza-1,3-butadiene]nickel dichloride,
1,4-bis(butylheptylamino)-1,4-diaza-1,3-butadiene]nickel dichloride,
1,4-bis(butyloctylamino)-1,4-diaza-1,3-butadiene]nickel dichloride,
1,4-bis(butylnonylamino)-1,4-diaza-1,3-butadiene]nickel dichloride,
1,4-bis(butyldecylamino)-1,4-diaza-1,3-butadiene]nickel dichloride,
1,4-bis(butylundecylamino)-1,4-diaza-1,3-butadiene]nickel dichloride,
1,4-bis(butyldodecylamino)-1,4-diaza-1,3-butadiene]nickel dichloride,
1,4-bis(butylcyclopentylamino)-1,4-diaza-1,3-butadiene] nickel dichloride,
1,4-bis(butylcyclohexylamino)-1,4-diaza-1,3-butadiene] nickel dichloride,
1,4-bis(butylcycloheptylamino)-1,4-diaza-1,3-butadiene] nickel dichloride,
1,4-bis(butylcyclooctylamino)-1,4-diaza-1,3-butadiene] nickel dichloride,
1,4-bis(butylcyclononylamino)-1,4-diaza-1,3-butadienelnickel dichloride,
1,4-bis(butylcyclodecylamino)-1,4-diaza-1,3-butadiene] nickel dichloride,
1,4-bis(butylcycloundecylamino)-1,4-diaza-1,3-butadiene] nickel dichloride,
1,4-bis(butylcyclododecylamino)-1,4-diaza-1,3-butadiene] nickel dichloride,
1,4-bis(pentylhexylamino)-1,4-diaza-1,3-butadiene]nickel dichloride,
1,4-bis(pentylheptylamino)-1,4-diaza-1,3-butadiene]nickel dichloride,
1,4-bis(pentyloctylamino)-1,4-diaza-1,3-butadiene]nickel dichloride,
1,4-bis(pentylnonylamino)-1,4-diaza-1,3-butadiene]nickel dichloride, 1,4-bis(pentyldecylamino)-1,4-diaza-1,3-butadiene]nickel dichloride,
1,4-bis(pentylundecylamino)-1,4-diaza-1,3-butadiene] nickel dichloride,
1,4-bis(pentyldodecylamino)-1,4-diaza-1,3-butadiene] nickel dichloride,
1,4-bis(pentylcyclopentylamino)-1,4-diaza-1,3-butadiene] nickel dichloride,
1,4-bis(pentylcyclohexylamino)-1,4-diaza-1,3-butadiene] nickel dichloride,
1,4-bis(pentylcycloheptylamino)-1,4-diaza-1,3-butadiene] nickel dichloride,
1,4-bis(pentylcyclooctylamino)-1,4-diaza-1,3-butadiene] nickel dichloride,
1,4-bis(pentylcyclononylamino)-1,4-diaza-1,3-butadiene] nickel dichloride,
1,4-bis(pentylcyclodecylamino)-1,4-diaza-1,3-butadiene] nickel dichloride,
1,4-bis(pentylcycloundecylamino)-1,4-diaza-1,3-butadiene] nickel dichloride,
1,4-bis(pentylcyclododecylamino)-1,4-diaza-1,3-butadiene] nickel dichloride,
1,4-bis(hexylheptylamino)-1,4-diaza-1,3-butadiene]nickel dichloride,
1,4-bis(hexyloctylamino)-1,4-diaza-1,3-butadiene]nickel dichloride,
1,4-bis(hexylnonylamino)-1,4-diaza-1,3-butadiene]nickel dichloride,
1,4-bis(hexyldecylamino)-1,4-diaza-1,3-butadiene]nickel dichloride,
1,4-bis(hexylundecylamino)-1,4-diaza-1,3-butadiene]nickel dichloride,
1,4-bis(hexyldodecylamino)-1,4-diaza-1,3-butadiene]nickel dichloride,
1,4-bis(hexylcyclopentylamino)-1,4-diaza-1,3-butadiene] nickel dichloride,
1,4-bis(hexylcyclohexylamino)-1,4-diaza-1,3-butadiene] nickel dichloride,
1,4-bis(hexylcyclohepylamino)-1,4-diaza-1,3-butadiene] nickel dichloride,
1,4-bis(hexylcyclooctylamino)-1,4-diaza-1,3-butadiene] nickel dichloride,
1,4-bis(hexylcyclononylamino)-1,4-diaza-1,3-butadiene] nickel dichloride,
1,4-bis(hexylcyclodecylamino)-1,4-diaza-1,3-butadiene] nickel dichloride,
1,4-bis(hexylcycloundecylamino)-1,4-diaza-1,3-butadiene] nickel dichloride,
1,4-bis(hexylcyclododecylamino)-1,4-diaza-1,3-butadiene] nickel dichloride,
1,4-bis(heptyloctylamino)-1,4-diaza-1,3-butadiene]nickel dichloride,
1,4-bis(heptylnonylamino)-1,4-diaza-1,3-butadiene]nickel dichloride,
1,4-bis(heptyldecylamino)-1,4-diaza-1,3-butadiene]nickel dichloride,
1,4-bis(heptylundecylamino)-1,4-diaza-1,3-butadiene] nickel dichloride,
1,4-bis(heptyldodecylamino)-1,4-diaza-1,3-butadiene] nickel dichloride,
1,4-bis(heptylcyclopentylamino)-1,4-diaza-1,3-butadiene] nickel dichloride,
1,4-bis(heptylcyclohexylamino)-1,4-diaza-1,3-butadiene] nickel dichloride,
1,4-bis(heptylcycloheptylamino)-1,4-diaza-1,3-butadiene] nickel dichloride,
1,4-bis(heptylcyclooctylamino)-1,4-diaza-1,3-butadiene] nickel dichloride,
1,4-bis(heptylcyclononylamino)-1,4-diaza-1,3-butadiene] nickel dichloride,
1,4-bis(heptylcyclodecylamino)-1,4-diaza-1,3-butadiene] nickel dichloride,
1,4-bis(heptylcycloundecylamino)-1,4-diaza-1,3-butadiene] nickel dichloride,
1,4-bis(heptylcyclododecylamino)-1,4-diaza-1,3-butadiene] nickel dichloride,
1,4-bis(octylnonylamino)-1,4-diaza-1,3-butadiene]nickel dichloride,
1,4-bis(octyldecylamino)-1,4-diaza-1,3-butadiene]nickel dichloride,
1,4-bis(octylundecylamino)-1,4-diaza-1,3-butadiene]nickel dichloride,
1,4-bis(octyldodecylamino)-1,4-diaza-1,3-butadiene]nickel dichloride,
1,4-bis(octylcyclopentylamino)-1,4-diaza-1,3-butadiene] nickel dichloride,
1,4-bis(octylcyclohexylamino)-1,4-diaza-1,3-butadiene] nickel dichloride,
1,4-bis(octylcycloheptylamino)-1,4-diaza-1,3-butadiene] nickel dichloride,
1,4-bis(octylcyclooctylamino)-1,4-diaza-1,3-butadiene] nickel dichloride,
1,4-bis(octylcyclononylamino)-1,4-diaza-1,3-butadiene] nickel dichloride,
1,4-bis(octylcyclodecylamino)-1,4-diaza-1,3-butadiene] nickel dichloride,
1,4-bis(octylcycloundecylamino)-1,4-diaza-1,3-butadiene] nickel dichloride,
1,4-bis(octylcyclododecylamino)-1,4-diaza-1,3-butadiene] nickel dichloride,
1,4-bis(nonyldecylamino)-1,4-diaza-1,3-butadiene]nickel dichloride,
1,4-bis(nonylundecylamino)-1,4-diaza-1,3-butadiene]nickel dichloride,
1,4-bis(nonyldodecylamino)-1,4-diaza-1,3-butadiene]nickel dichloride,
1,4-bis(nonylcyclopentylamino)-1,4-diaza-1,3-butadiene] nickel dichloride,
1,4-bis(nonylcyclohexylamino)-1,4-diaza-1,3-butadiene] nickel dichloride,
1,4-bis(nonylcycloheptylamino)-1,4-diaza-1,3-butadiene] nickel dichloride,
1,4-bis(nonylcyclooctylamino)-1,4-diaza-1,3-butadiene] nickel dichloride,
1,4-bis(nonylcyclononylamino)-1,4-diaza-1,3-butadiene] nickel dichloride,
1,4-bis(nonylcyclodecylamino)-1,4-diaza-1,3-butadiene] nickel dichloride,
1,4-bis(nonylcycloundecylamino)-1,4-diaza-1,3-butadiene] nickel dichloride,
1,4-bis(nonylcyclododecylamino)-1,4-diaza-1,3-butadiene] nickel dichloride,
1,4-bis(decylundecylamino)-1,4-diaza-1,3-butadiene]nickel dichloride,
1,4-bis(decyldodecylamino)-1,4-diaza-1,3-butadiene]nickel dichloride,
1,4-bis(decylcyclopentylamino)-1,4-diaza-1,3-butadiene] nickel dichloride,
1,4-bis(decylcyclohexylamino)-1,4-diaza-1,3-butadiene] nickel dichloride,
1,4-bis(decylcycloheptylamino)-1,4-diaza-1,3-butadiene] nickel dichloride, 1,4-bis(decylcyclooctylamino)-1,4-diaza-1,3-butadiene]
nickel dichloride,
1,4-bis(decylcyclononylamino)-1,4-diaza-1,3-butadiene]
nickel dichloride,
1,4-bis(decylcyclodecylamino)-1,4-diaza-1,3-butadiene]
nickel dichloride,
1,4-bis(decylcycloundecylamino)-1,4-diaza-1,3-butadiene]
nickel dichloride,
1,4-bis(decylcyclododecylamino)-1,4-diaza-1,3-butadienelnickel dichloride,
1,4-bis(undecyldodecylamino)-1,4-diaza-1,3-butadiene]
nickel dichloride,
1,4-bis(undecylcyclopentylamino)-1,4-diaza-1,3-butadiene]
nickel dichloride,
1,4-bis(undecylcyclohexylamino)-1,4-diaza-1,3-butadiene]
nickel dichloride,
1,4-bis(undecylcycloheptylamino)-1,4-diaza-1,3-butadiene]
nickel dichloride,
1,4-bis(undecylcyclooctylamino)-1,4-diaza-1,3-butadiene]
nickel dichloride,
1,4-bis(undecylcyclononylamino)-1,4-diaza-1,3-butadiene]
nickel dichloride,
1,4-bis(undecylcyclodecylamino)-1,4-diaza-1,3-butadiene]
nickel dichloride,
1,4-bis(undecylcycloundecylamino)-1,4-diaza-1,3-butadienelnickel dichloride,
1,4-bis(undecylcyclododecylamino)-1,4-diaza-1,3-butadiene]nickel dichloride,
1,4-bis(dodecylcyclopentylamino)-1,4-diaza-1,3-butadiene]
nickel dichloride,
1,4-bis(dodecylcyclohexylamino)-1,4-diaza-1,3-butadiene]
nickel dichloride,
1,4-bis(dodecylcycloheptylamino)-1,4-diaza-1,3-butadiene]
nickel dichloride,
1,4-bis(dodecylcyclooctylamino)-1,4-diaza-1,3-butadiene]
nickel dichloride,
1,4-bis(dodecylcyclononylamino)-1,4-diaza-1,3-butadiene]
nickel dichloride,
1,4-bis(dodecylcyclodecylamino)-1,4-diaza-1,3-butadiene]
nickel dichloride,
1,4-bis(dodecylcycloundecylamino)-1,4-diaza-1,3-butadiene]nickel dichloride,
1,4-bis(dodecylcyclododecylamino)-1,4-diaza-1,3-butadiene]nickel dichloride,
1,4-bis(cyclopentylcyclohexylamino)-1,4-diaza-1,3-butadiene]nickel dichloride,
1,4-bis(cyclopentylcycloheptylamino)-1,4-diaza-1,3-butadiene]nickel dichloride,
1,4-bis(cyclopentylcyclooctylamino)-1,4-diaza-1,3-butadiene]nickel dichloride,
1,4-bis(cyclopentylcyclononylamino)-1,4-diaza-1,3-butadiene]nickel dichloride,
1,4-bis(cyclopentylcyclodecylamino)-1,4-diaza-1,3-butadiene]nickel dichloride,
1,4-bis(cyclopentylcycloundecylamino)-1,4-diaza-1,3-butadiene]nickel dichloride,
1,4-bis(cyclopentylcyclododecylamino)-1,4-diaza-1,3-butadiene]nickel dichloride,
1,4-bis(cyclohexylcycloheptylamino)-1,4-diaza-1,3-butadiene]nickel dichloride,
1,4-bis(cyclohexylcyclooctylamino)-1,4-diaza-1,3-butadiene]nickel dichloride,
1,4-bis(cyclohexylcyclononylamino)-1,4-diaza-1,3-butadiene]nickel dichloride,
1,4-bis(cyclohexylcyclodecylamino)-1,4-diaza-1,3-butadiene]nickel dichloride,
1,4-bis(cyclohexylcycloundecylamino)-1,4-diaza-1,3-butadiene]nickel dichloride,
1,4-bis(cyclohexylcyclododecylamino)-1,4-diaza-1,3-butadiene]nickel dichloride,
1,4-bis(cycloheptylcyclooctylamino)-1,4-diaza-1,3-butadiene]nickel dichloride,
1,4-bis(cycloheptylcyclononylamino)-1,4-diaza-1,3-butadiene]nickel dichloride,
1,4-bis(cycloheptylcyclodecylamino)-1,4-diaza-1,3-butadiene]nickel dichloride,
1,4-bis(cycloheptylcycloundecylamino)-1,4-diaza-1,3-butadiene]nickel dichloride,
1,4-bis(cycloheptylcyclododecylamino)-1,4-diaza-1,3-butadiene]nickel dichloride,
1,4-bis(cyclooctylcyclononylamino)-1,4-diaza-1,3-butadiene]nickel dichloride,
1,4-bis(cyclooctylcyclodecylamino)-1,4-diaza-1,3-butadiene]nickel dichloride,
1,4-bis(cyclooctylcycloundecylamino)-1,4-diaza-1,3-butadiene]nickel dichloride,
1,4-bis(cyclooctylcyclododecylamino)-1,4-diaza-1,3-butadiene]nickel dichloride,
1,4-bis(cyclononylcyclodecylamino)-1,4-diaza-1,3-butadiene]nickel dichloride,
1,4-bis(cyclononylcycloundecylamino)-1,4-diaza-1,3-butadiene]nickel dichloride,
1,4-bis(cyclononylcyclododecylamino)-1,4-diaza-1,3-butadiene]nickel dichloride,
1,4-bis(cyclodecylcycloundecylamino)-1,4-diaza-1,3-butadiene]nickel dichloride,
1,4-bis(cyclodecylcyclododecylamino)-1,4-diaza-1,3-butadiene]nickel dichloride, and 1,4-bis(cycloundecylcyclododecylamino)-1,4-diaza-1, 3-butadiene]nickel dichloride.

Examples of compounds with unsymmetrical ligand structures not containing heteroalicyclic ring structures include:
1-(dipropylamino)-4-(diethylamino)-1,4-diaza-1,3-butadiene]nickel dichloride,
1-(dibutylamino)-4-(diethylamino)-1,4-diaza-1,3-butadiene]nickel dichloride,
1-(dipentylamino)-4-(diethylamino)-1,4-diaza-1,3-butadiene]nickel dichloride,
1-(dihexylamino)-4-(diethylamino)-1,4-diaza-1,3-butadiene]nickel dichloride,
1-(diheptylamino)-4-(diethylamino)-1,4-diaza-1,3-butadiene]nickel dichloride,
1-(dioctylamino)-4-(diethylamino)-1,4-diaza-1,3-butadiene]nickel dichloride,
1-(dinonylamino)-4-(diethylamino)-1,4-diaza-1,3-butadiene]nickel dichloride,
1-(didecylamino)-4-(diethylamino)-1,4-diaza-1,3-butadiene]nickel dichloride,
1-(diundecylamino)-4-(diethylamino)-1,4-diaza-1,3-butadiene]nickel dichloride,
1-(didodecylamino)-4-(diethylamino)-1,4-diaza-1,3-butadiene]nickel dichloride,
1-(dicyclopentylamino)-4-(diethylamino)-1,4-diaza-1,3-butadiene]nickel dichloride,
1-(dicyclohexylamino)-4-(diethylamino)-1,4-diaza-1,3-butadiene]nickel dichloride,
1-(dicyclohepylamino)-4-(diethylamino)-1,4-diaza-1,3-butadiene]nickel dichloride,
1-(dicyclooctylamino)-4-(diethylamino)-1,4-diaza-1,3-butadiene]nickel dichloride, 1-(dicyclononylamino)-4-(diethylamino)-1,4-diaza-1,3-butadiene]nickel dichloride,
1-(dicyclodecylamino)-4-(diethylamino)-1,4-diaza-1,3-butadiene]nickel dichloride,
1-(dicycloundecylamino)-4-(diethylamino)-1,4-diaza-1,3-butadiene]nickel dichloride,
1-(dicyclododecylamino)-4-(diethylamino)-1,4-diaza-1,3-butadiene]nickel dichloride,
1-(dibutylamino)-4-(dipropylamino)-1,4-diaza-1,3-butadiene]nickel dichloride,
1-(dipentylamino)-4-(dipropylamino)-1,4-diaza-1,3-butadiene]nickel dichloride,
1-(dihexylamino)-4-(dipropylamino)-1,4-diaza-1,3-butadiene]nickel dichloride,
1-(diheptylamino)-4-(dipropylamino)-1,4-diaza-1,3-butadiene]nickel dichloride,
1-(dioctylamino)-4-(dipropylamino)-1,4-diaza-1,3-butadiene]nickel dichloride,
1-(dinonylamino)-4-(dipropylamino)-1,4-diaza-1,3-butadiene]nickel dichloride,
1-(didecylamino)-4-(dipropylamino)-1,4-diaza-1,3-butadiene]nickel dichloride,
1-(diundecylamino)-4-(dipropylamino)-1,4-diaza-1,3-butadiene]nickel dichloride,
1-(didodecylamino)-4-(dipropylamino)-1,4-diaza-1,3-butadiene]nickel dichloride,
1-(dicyclopentylamino)-4-(dipropylamino)-1,4-diaza-1,3-butadiene]nickel dichloride,
1-(dicyclohexylamino)-4-(dipropylamino)-1,4-diaza-1,3-butadiene]nickel dichloride,
1-(dicyclohepylamino)-4-(dipropylamino)-1,4-diaza-1,3-butadiene]nickel dichloride,
1-(dicyclooctylamino)-4-(dipropylamino)-1,4-diaza-1,3-butadiene]nickel dichloride,
1-(dicyclononylamino)-4-(dipropylamino)-1,4-diaza-1,3-butadiene]nickel dichloride,
1-(dicyclodecylamino)-4-(dipropylamino)-1,4-diaza-1,3-butadiene]nickel dichloride,
1-(dicycloundecylamino)-4-(dipropylamino)-1,4-diaza-1,3-butadiene]nickel dichloride,
1-(dicyclododecylamino)-4-(dipropylamino)-1,4-diaza-1,3-butadiene]nickel dichloride,
1-(dipentylamino)-4-(dibutylamino)-1,4-diaza-1,3-butadiene]nickel dichloride,
1-(dihexylamino)-4-(dibutylamino)-1,4-diaza-1,3-butadiene]nickel dichloride,
1-(diheptylamino)-4-(dibutylamino)-1,4-diaza-1,3-butadiene]nickel dichloride,
1-(dioctylamino)-4-(dibutylamino)-1,4-diaza-1,3-butadiene]nickel dichloride,
1-(dinonylamino)-4-(dibutylamino)-1,4-diaza-1,3-butadiene]nickel dichloride,
1-(didecylamino)-4-(dibutylamino)-1,4-diaza-1,3-butadiene]nickel dichloride,
1-(diundecylamino)-4-(dibutylamino)-1,4-diaza-1,3-butadiene]nickel dichloride,
1-(didodecylamino)-4-(dibutylamino)-1,4-diaza-1,3-butadiene]nickel dichloride,
1-(dicyclopentylamino)-4-(dibutylamino)-1,4-diaza-1,3-butadiene]nickel dichloride,
1-(dicyclohexylamino)-4-(dibutylamino)-1,4-diaza-1,3-butadiene]nickel dichloride,
1-(dicyclohepylamino)-4-(dibutylamino)-1,4-diaza-1,3-butadiene]nickel dichloride,
1-(dicyclooctylamino)-4-(dibutylamino)-1,4-diaza-1,3-butadiene]nickel dichloride,
1-(dicyclononylamino)-4-(dibutylamino)-1,4-diaza-1,3-butadiene]nickel dichloride,
1-(dicyclodecylamino)-4-(dibutylamino)-1,4-diaza-1,3-butadiene]nickel dichloride,
1-(dicycloundecylamino)-4-(dibutylamino)-1,4-diaza-1,3-butadiene]nickel dichloride,
1-(dicyclododecylamino)-4-(dibutylamino)-1,4-diaza-1,3-butadiene]nickel dichloride,
1-(dihexylamino)-4-(dipentylamino)-1,4-diaza-1,3-butadiene]nickel dichloride,
1-(diheptylamino)-4-(dipentylamino)-1,4-diaza-1,3-butadiene]nickel dichloride,
1-(dioctylamino)-4-(dipentylamino)-1,4-diaza-1,3-butadiene]nickel dichloride,
1-(dinonylamino)-4-(dipentylamino)-1,4-diaza-1,3-butadiene]nickel dichloride,
1-(didecylamino)-4-(dipentylamino)-1,4-diaza-1,3-butadiene]nickel dichloride,
1-(diundecylamino)-4-(dipentylamino)-1,4-diaza-1,3-butadiene]nickel dichloride,
1-(didodecylamino)-4-(dipentylamino)-1,4-diaza-1,3-butadiene]nickel dichloride,
1-(dicyclopentylamino)-4-(dipentylamino)-1,4-diaza-1,3-butadiene]nickel dichloride,
1-(dicyclohexylamino)-4-(dipentylamino)-1,4-diaza-1,3-butadiene]nickel dichloride,
1-(dicyclohepylamino)-4-(dipentylamino)-1,4-diaza-1,3-butadiene]nickel dichloride,
1-(dicyclooctylamino)-4-(dipentylamino)-1,4-diaza-1,3-butadiene]nickel dichloride,
1-(dicyclononylamino)-4-(dipentylamino)-1,4-diaza-1,3-butadiene]nickel dichloride,
1-(dicyclodecylamino)-4-(dipentylamino)-1,4-diaza-1,3-butadiene]nickel dichloride,
1-(dicycloundecylamino)-4-(dipentylamino)-1,4-diaza-1,3-butadiene]nickel dichloride,
1-(dicyclododecylamino)-4-(dipentylamino)-1,4-diaza-1,3-butadiene]nickel dichloride,
1-(diheptylamino)-4-(dihexylamino)-1,4-diaza-1,3-butadiene]nickel dichloride,
1-(dioctylamino)-4-(dihexylamino)-1,4-diaza-1,3-butadiene]nickel dichloride,
1-(dinonylamino)-4-(dihexylamino)-1,4-diaza-1,3-butadiene]nickel dichloride,
1-(didecylamino)-4-(dihexylamino)-1,4-diaza-1,3-butadiene]nickel dichloride,
1-(diundecylamino)-4-(dihexylamino)-1,4-diaza-1,3-butadiene]nickel dichloride,
1-(didodecylamino)-4-(dihexylamino)-1,4-diaza-1,3-butadiene]nickel dichloride,
1-(dicyclopentylamino)-4-(dihexylamino)-1,4-diaza-1,3-butadiene]nickel dichloride,
1-(dicyclohexylamino)-4-(dihexylamino)-1,4-diaza-1,3-butadiene]nickel dichloride,
1-(dicyclohepylamino)-4-(dihexylamino)-1,4-diaza-1,3-butadiene]nickel dichloride,
1-(dicyclooctylamino)-4-(dihexylamino)-1,4-diaza-1,3-butadiene]nickel dichloride,
1-(dicyclononylamino)-4-(dihexylamino)-1,4-diaza-1,3-butadiene]nickel dichloride,
1-(dicyclodecylamino)-4-(dihexylamino)-1,4-diaza-1,3-butadiene]nickel dichloride,
1-(dicycloundecylamino)-4-(dihexylamino)-1,4-diaza-1,3-butadiene]nickel dichloride,
1-(dicyclododecylamino)-4-(dihexylamino)-1,4-diaza-1,3-butadiene]nickel dichloride, 1-(dioctylamino)-4-(diheptylamino)-1,4-diaza-1,3-butadiene]nickel dichloride,
1-(dinonylamino)-4-(diheptylamino)-1,4-diaza-1,3-butadiene]nickel dichloride,
1-(didecylamino)-4-(diheptylamino)-1,4-diaza-1,3-butadiene]nickel dichloride,
1-(diundecylamino)-4-(diheptylamino)-1,4-diaza-1,3-butadiene]nickel dichloride,
1-(didodecylamino)-4-(diheptylamino)-1,4-diaza-1,3-butadiene]nickel dichloride,
1-(dicyclopentylamino)-4-(diheptylamino)-1,4-diaza-1,3-butadiene]nickel dichloride,
1-(dicyclohexylamino)-4-(diheptylamino)-1,4-diaza-1,3-butadiene]nickel dichloride,
1-(dicyclohepylamino)-4-(diheptylamino)-1,4-diaza-1,3-butadiene]nickel dichloride,
1-(dicyclooctylamino)-4-(diheptylamino)-1,4-diaza-1,3-butadiene]nickel dichloride,
1-(dicyclononylamino)-4-(diheptylamino)-1,4-diaza-1,3-butadiene]nickel dichloride,
1-(dicyclodecylamino)-4-(diheptylamino)-1,4-diaza-1,3-butadiene]nickel dichloride,
1-(dicycloundecylamino)-4-(diheptylamino)-1,4-diaza-1,3-butadiene]nickel dichloride,
1-(dicyclododecylamino)-4-(diheptylamino)-1,4-diaza-1,3-butadiene]nickel dichloride,
1-(dinonylamino)-4-(dioctylamino)-1,4-diaza-1,3-butadiene]nickel dichloride,
1-(didecylamino)-4-(dioctylamino)-1,4-diaza-1,3-butadiene]nickel dichloride,
1-(diundecylamino)-4-(dioctylamino)-1,4-diaza-1,3-butadiene]nickel dichloride,
1-(didodecylamino)-4-(dioctylamino)-1,4-diaza-1,3-butadiene]nickel dichloride,
1-(dicyclopentylamino)-4-(dioctylamino)-1,4-diaza-1,3-butadiene]nickel dichloride,
1-(dicyclohexylamino)-4-(dioctylamino)-1,4-diaza-1,3-butadiene]nickel dichloride,
1-(dicyclohepylamino)-4-(dioctylamino)-1,4-diaza-1,3-butadiene]nickel dichloride,
1-(dicyclooctylamino)-4-(dioctylamino)-1,4-diaza-1,3-butadiene]nickel dichloride,
1-(dicyclononylamino)-4-(dioctylamino)-1,4-diaza-1,3-butadiene]nickel dichloride,
1-(dicyclodecylamino)-4-(dioctylamino)-1,4-diaza-1,3-butadiene]nickel dichloride,
1-(dicycloundecylamino)-4-(dioctylamino)-1,4-diaza-1,3-butadiene]nickel dichloride,
1-(dicyclododecylamino)-4-(dioctylamino)-1,4-diaza-1,3-butadiene]nickel dichloride,
1-(didecylamino)-4-(dinonylamino)-1,4-diaza-1,3-butadiene]nickel dichloride,
1-(diundecylamino)-4-(dinonylamino)-1,4-diaza-1,3-butadiene]nickel dichloride,
1-(didodecylamino)-4-(dinonylamino)-1,4-diaza-1,3-butadiene]nickel dichloride,
1-(dicyclopentylamino)-4-(dinonylamino)-1,4-diaza-1,3-butadiene]nickel dichloride,
1-(dicyclohexylamino)-4-(dinonylamino)-1,4-diaza-1,3-butadiene]nickel dichloride,
1-(dicyclohepylamino)-4-(dinonylamino)-1,4-diaza-1,3-butadiene]nickel dichloride,
1-(dicyclooctylamino)-4-(dinonylamino)-1,4-diaza-1,3-butadiene]nickel dichloride,
1-(dicyclononylamino)-4-(dinonylamino)-1,4-diaza-1,3-butadiene]nickel dichloride,
1-(dicyclodecylamino)-4-(dinonylamino)-1,4-diaza-1,3-butadiene]nickel dichloride,
1-(dicycloundecylamino)-4-(dinonylamino)-1,4-diaza-1,3-butadiene]nickel dichloride,
1-(dicyclododecylamino)-4-(dinonylamino)-1,4-diaza-1,3-butadiene]nickel dichloride,
1-(diundecylamino)-4-(didecylamino)-1,4-diaza-1,3-butadiene]nickel dichloride,
1-(didodecylamino)-4-(didecylamino)-1,4-diaza-1,3-butadiene]nickel dichloride,
1-(dicyclopentylamino)-4-(didecylamino)-1,4-diaza-1,3-butadiene]nickel dichloride,
1-(dicyclohexylamino)-4-(didecylamino)-1,4-diaza-1,3-butadiene]nickel dichloride,
1-(dicyclohepylamino)-4-(didecylamino)-1,4-diaza-1,3-butadiene]nickel dichloride,
1-(dicyclooctylamino)-4-(didecylamino)-1,4-diaza-1,3-butadiene]nickel dichloride,
1-(dicyclononylamino)-4-(didecylamino)-1,4-diaza-1,3-butadiene]nickel dichloride,
1-(dicyclodecylamino)-4-(didecylamino)-1,4-diaza-1,3-butadiene]nickel dichloride,
1-(dicycloundecylamino)-4-(didecylamino)-1,4-diaza-1,3-butadiene]nickel dichloride,
1-(dicyclododecylamino)-4-(didecylamino)-1,4-diaza-1,3-butadiene]nickel dichloride,
1-(didodecylamino)-4-(diundecylamino)-1,4-diaza-1,3-butadiene]nickel dichloride,
1-(dicyclopentylamino)-4-(diundecylamino)-1,4-diaza-1,3-butadiene]nickel dichloride,
1-(dicyclohexylamino)-4-(diundecylamino)-1,4-diaza-1,3-butadiene]nickel dichloride,
1-(dicyclohepylamino)-4-(diundecylamino)-1,4-diaza-1,3-butadiene]nickel dichloride,
1-(dicyclooctylamino)-4-(diundecylamino)-1,4-diaza-1,3-butadiene]nickel dichloride,
1-(dicyclononylamino)-4-(diundecylamino)-1,4-diaza-1,3-butadiene]nickel dichloride,
1-(dicyclodecylamino)-4-(diundecylamino)-1,4-diaza-1,3-butadiene]nickel dichloride,
1-(dicycloundecylamino)-4-(diundecylamino)-1,4-diaza-1,3-butadiene]nickel dichloride,
1-(dicyclododecylamino)-4-(diundecylamino)-1,4-diaza-1,3-butadiene]nickel dichloride,
1-(dicyclopentylamino)-4-(didodecylamino)-1,4-diaza-1,3-butadiene]nickel dichloride,
1-(dicyclohexylamino)-4-(didodecylamino)-1,4-diaza-1,3-butadiene]nickel dichloride,
1-(dicyclohepylamino)-4-(didodecylamino)-1,4-diaza-1,3-butadiene]nickel dichloride,
1-(dicyclooctylamino)-4-(didodecylamino)-1,4-diaza-1,3-butadiene]nickel dichloride,
1-(dicyclononylamino)-4-(didodecylamino)-1,4-diaza-1,3-butadiene]nickel dichloride,
1-(dicyclodecylamino)-4-(didodecylamino)-1,4-diaza-1,3-butadiene]nickel dichloride,
1-(dicycloundecylamino)-4-(didodecylamino)-1,4-diaza-1,3-butadiene]nickel dichloride,
1-(dicyclododecylamino)-4-(didodecylamino)-1,4-diaza-1,3-butadiene]nickel dichloride,
1-(dicyclohexylamino)-4-(dicyclopentylamino)-1,4-diaza-1,3-butadiene]nickel dichloride,
1-(dicyclohepylamino)-4-(dicyclopentylamino)-1,4-diaza-1,3-butadiene]nickel dichloride,
1-(dicyclooctylamino)-4-(dicyclopentylamino)-1,4-diaza-1,3-butadiene]nickel dichloride, 1-(dicyclononylamino)-4-(dicyclopentylamino)-1,4-diaza-1,3-butadiene]nickel dichloride,
1-(dicyclodecylamino)-4-(dicyclopentylamino)-1,4-diaza-1,3-butadiene]nickel dichloride,
1-(dicycloundecylamino)-4-(dicyclopentylamino)-1,4-diaza-1,3-butadiene]nickel dichloride,
1-(dicyclododecylamino)-4-(dicyclopentylamino)-1,4-diaza-1,3-butadiene]nickel dichloride,
1-(dicyclohepylamino)-4-(dicyclohexylamino)-1,4-diaza-1,3-butadiene]nickel dichloride,
1-(dicyclooctylamino)-4-(dicyclohexylamino)-1,4-diaza-1,3-butadiene]nickel dichloride,
1-(dicyclononylamino)-4-(dicyclohexylamino)-1,4-diaza-1,3-butadiene]nickel dichloride,
1-(dicyclodecylamino)-4-(dicyclohexylamino)-1,4-diaza-1,3-butadiene]nickel dichloride,
1-(dicycloundecylamino)-4-(dicyclohexylamino)-1,4-diaza-1,3-butadiene]nickel dichloride,
1-(dicyclododecylamino)-4-(dicyclohexylamino)-1,4-diaza-1,3-butadiene]nickel dichloride,
1-(dicyclooctylamino)-4-(dicycloheptylamino)-1,4-diaza-1,3-butadiene]nickel dichloride,
1-(dicyclononylamino)-4-(dicycloheptylamino)-1,4-diaza-1,3-butadiene]nickel dichloride,
1-(dicyclodecylamino)-4-(dicycloheptylamino)-1,4-diaza-1,3-butadiene]nickel dichloride,
1-(dicycloundecylamino)-4-(dicycloheptylamino)-1,4-diaza-1,3-butadiene]nickel dichloride,
1-(dicyclododecylamino)-4-(dicycloheptylamino)-1,4-diaza-1,3-butadiene]nickel dichloride,
1-(dicyclononylamino)-4-(dicyclooctylamino)-1,4-diaza-1,3-butadiene]nickel dichloride,
1-(dicyclodecylamino)-4-(dicyclooctylamino)-1,4-diaza-1,3-butadiene]nickel dichloride,
1-(dicycloundecylamino)-4-(dicyclooctylamino)-1,4-diaza-1,3-butadiene]nickel dichloride,
1-(dicyclododecylamino)-4-(dicyclooctylamino)-1,4-diaza-1,3-butadiene]nickel dichloride,
1-(dicyclodecylamino)-4-(dicyclononylamino)-1,4-diaza-1,3-butadiene]nickel dichloride,
1-(dicycloundecylamino)-4-(dicyclononylamino)-1,4-diaza-1,3-butadiene]nickel dichloride,
1-(dicyclododecylamino)-4-(dicyclononylamino)-1,4-diaza-1,3-butadiene]nickel dichloride,
1-(dicycloundecylamino)-4-(dicyclodecylamino)-1,4-diaza-1,3-butadiene]nickel dichloride,
1-(dicyclododecylamino)-4-(dicyclodecylamino)-1,4-diaza-1,3-butadiene]nickel dichloride, and
1-(dicyclododecylamino)-4-(dicycloundecylamino)-1,4-diaza-1,3-butadiene]nickel dichloride.

A similar list of platinum and palladium compounds can be generated by replacing "nickel" with "platinum" or "palladium".

EXAMPLES

The following examples are presented to illustrate the discussion above. Although the examples may be directed toward certain embodiments of the present invention, they do not limit the invention in any specific way. In these examples, certain abbreviations are used to facilitate the description. These include standard chemical abbreviations for the elements and certain commonly accepted abbreviations, such as: Me=methyl, Et=ethyl, Bu=butyl, Ph=phenyl, MAO=methylalumoxane, DAB=diazabutadiene, DAB(Me)$_2$=2,3-dimethyldiazabutadiene, COD=cyclooctadiene and DME=ethylene glycol dimethyl ether.

All preparations were performed under an inert nitrogen atmosphere, using standard Schlenk or glovebox techniques, unless mentioned otherwise. Dry solvents (toluene, diethyl ether, pentane, methylene chloride) were purchased as anhydrous solvents and further purified by passing them down an alumina (Fluka) column. Ethylene was purchased from BOC (99.9%). 3A molecular sieves (1.6 mm pellets), formic acid (96%), methanol, 1-aminohomopiperidine, 1-aminopiperidine, 2,3-butanedione, magnesium sulfate, nickel(II) bromide ethylene glycol dimethylether complex, and dichloro (1,5-cyclooctadiene)palladium(II) were purchased from Aldrich Chemical Company. Deuterated solvents were dried with CaH and vacuum distilled prior to use. The compounds are illustrated below.

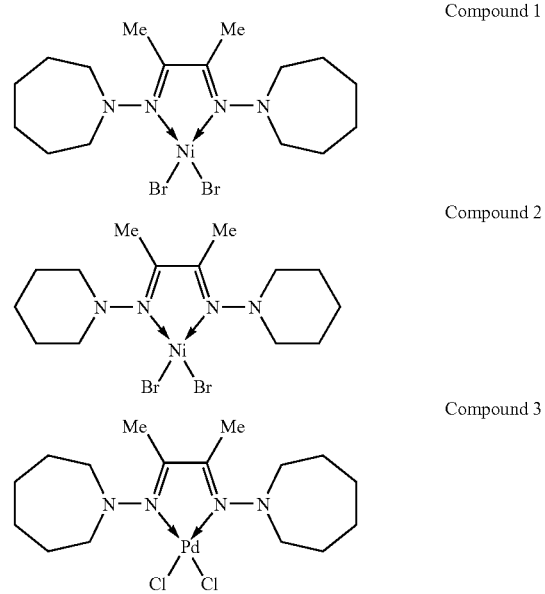

Compound 1

Compound 2

Compound 3

Preparation of the ligand, (c-C$_6$H$_{12}$N)—N═C(Me)C(Me)═N-(c-C$_6$H$_{12}$N). 1-aminohomopiperidine (20 g, 0.175 mol), methanol (30 ml) and formic acid (2 drops) were mixed together at 0° C. The mixture was warmed to room temperature and 3A molecular sieves were added. 2,3-butanedione (5.7 ml, 0.065 mol) was slowly added. The reaction mixture was stirred at room temperature for about 3 days. The mixture was filtered to remove the molecular sieves, and the resulting filtrate was reduced in volume and placed in a freezer at −30 C overnight. After filtration of the chilled mixture, yellow crystals of (c-C$_6$H$_{12}$N)—N═C(Me)C(Me)═N-(c-C$_6$H$_{12}$N) were obtained in a yield of 59.2%.

Preparation of [(c-C$_6$H$_{12}$N)$_2$DAB(Me)$_2$]NiBr$_2$ (1). CH$_2$Cl$_2$ (25 ml) was added to a flask containing (c-C$_6$H$_{12}$N)—N═C(Me)C(Me)═N-(c-C$_6$H$_{12}$N) (2.42 g, 8.70 mmol). A bright yellow solution was formed. This solution was added to a mixture of (DME)NiBr$_2$ (2.02 g, 6.54 mmol) suspended in CH$_2$Cl$_2$. Immediately a brown solution was formed upon mixing. The resulting brown solution was stirred for 20 hours. The solution was filtered twice and the resulting filtrate was reduced in volume to the point where solids began to precipitate out. Pentane was added and a large volume of red-brown solid precipitated. The solid was filtered, washed twice with pentane, and dried. The red-brown powder, [(c-C$_6$H$_{12}$N)—N═C(Me)C(Me)═N-(c-C$_6$H$_{12}$N)]NiBr$_2$, was isolated in 64.2% yield. The product was soluble in CH$_2$Cl$_2$. $^1$H NMR indicates that the complex is paramagnetic. Anal. Calcd for $(C_{16}H_{30}N_4Br_2Ni)$: C, 38.67%; H, 6.10%; N, 11.28%. Found: C, 38.70%; H, 6.44%; N, 11.33%. The IR (cm$^{-1}$, KBr): 1591, $\nu$(C=N); 272, $\nu$(Ni—Br). Orange colored crystals of the complex were grown from methylene chloride and an x-ray crystal structure was obtained.

Preparation of the ligand, (c-$C_5H_{10}$N)—N=C(Me)C(Me)=N-(c-$C_5H_{10}$N). 1-aminopiperidine (17.5 g, 0.175 mol), methanol (30 ml), formic acid (2 drops) and 3A molecular sieves were mixed together at 0° C. The mixture was warmed to ambient temperature and 2,3-butanedione (5.7 ml, 0.065 mol) was slowly added. The reaction mixture was stirred at room temperature for about 3 days. The mixture was filtered to remove the molecular sieves, and some anhydrous magnesium sulfate was added to the filtrate to further dry it. The mixture was then filtered to remove the magnesium sulfate. The filtrate was reduced in volume and was placed in a freezer at −30° C. for the weekend.

After filtration of the chilled mixture, yellow crystals of (c-$C_5H_{10}$N)—N=C(Me)C(Me)=N-(c-$C_5H_{10}$N) were obtained.

Preparation of [(c-$C_5H_{10}$N)$_2$DAB(Me)$_2$]NiBr$_2$ (2). CH$_2$Cl$_2$ (25 ml) was added to a flask containing (c-$C_5H_{10}$N)—N=C(Me)C(Me)=N-(c-$C_5H_{10}$N) (2.18 g, 8.70 mmol). A bright yellow solution was formed. This solution was added to a mixture of (DME)NiBr$_2$ (2.02 g, 6.54 mmol) suspended in CH$_2$Cl$_2$. Immediately a brown solution was formed upon mixing. The resulting brown solution was stirred for 20 hours. The solution was filtered twice and the resulting filtrate was reduced in volume to the point where solids began to precipitate out. Pentane was added and a large volume of red-brown solid precipitated. The solid was filtered, washed twice with pentane, and dried. A brown powder was isolated in 68.4% yield. The brown product was soluble in CH$_2$Cl$_2$. $^1$H NMR indicates that the complex is paramagnetic. Anal. Calcd for $(C_{14}H_{26}N_4Br_2Ni)$: C, 35.86%; H, 5.60%; N, 11.95%. Found: C, 35.64%; H, 5.45%; N, 11.99%. The IR (cm$^{-1}$, KBr): 1608, $\nu$(C=N); 275, $\nu$(Ni—Br)). Red-orange colored crystals of the complex were grown from methylene chloride and a x-ray crystal structure was obtained.

Preparation of [(c-$C_6H_{12}$N)$_2$DAB(Me)$_2$]PdCl$_2$ (3). Et$_2$O (40 ml) was added to a Schlenk flask containing a mixture of (c-$C_6H_{12}$N)—N=C(Me)C(Me)=N-(c-$C_6H_{12}$N) (1.21 g, 4.3 mmol) and (COD)PdCl$_2$ (1.14 g, 4.0 mmol) in a dry box. The reaction mixture was stirred overnight and then filtered. A red orange solution was obtained. The Et$_2$O solvent was removed in vacuo. The orange powder (which is a mixture of starting materials and product) was then redissolved in 20 ml of CH$_2$Cl$_2$. An additional amount of (c-$C_6H_{12}$N)—N=C(Me)C(Me)=N-(c-$C_6H_{12}$N) was added. (1.0 g, 3.6 mmol) and the mixture was allowed to stir overnight. To the dark red solution, pentane was added which precipitated out a dark orange solid which was filtered off and washed twice with additional pentane, and then dried in vacuo. An orange powder was isolated in 80.6% yield. The orange product was soluble in both CH$_2$Cl$_2$ and Et$_2$O. $^1$H NMR indicates that the complex is diamagnetic. $^1$H NMR (250 MHz, CD$_2$Cl$_2$, $\delta$, ppm): 1.60–1.73 m (16H, 8×CH$_2$); 2.33 s (6H, 2×CH$_3$); 3.44 t (8H, 4×CH$_2$). Anal. Calcd for $(C_{16}H_{30}N_4Cl_2Pd)$: C, 42.16%; H, 6.65%; N, 12.30%. Found: C, 40.31%; H, 6.41%; N, 11.69%.

Oligomerization Reactions

Oligomerization reactions were run in a 300-mL HastelloyC Parr reactor equipped with a mechanical stirrer. Catalyst was added to the reactor as a solution in toluene (75 ml) under argon. Ethylene was added to the reactor at 100 psig and then vented to maintain an ethylene atmosphere. Methylalumoxane solution (Albemarle, 30 wt % in toluene) was then added to the reactor. Thus, the catalyst was activated in the monomer's presence. The ethylene pressure was brought to the desired value. The aim was to maintain the reactor temperature at room temperature; but in cases where the reaction exotherm was very large, higher reaction temperatures were reached. After the reaction had run for an hour, the reactor was cooled in an acetone/dry ice bath, vented, and quenched with methanol. A sample of the product solution was analyzed by GC/MS after adding nonane as an internal standard. The results of the oligomerization reactions are tabulated in Table 2.

TABLE 2

Oligomerization Examples

| Example | Pre-catalyst[a] | Activity (mol C2/mol Ni · hr) | C2 (psig) | T (° C.) | Product-Olefins |
|---|---|---|---|---|---|
| 1 | 2 | 182,900 | 820 | 40 | C$_4$ & C$_6$ |
| 2 | 2 | 65,700 | 100 | 36 | C$_4$ & C$_6$ |
| 3 | 1 | 23,300 | 100 | 32 | C$_4$ & C$_6$ |
| 4 | 1 | 249,000 | 800 | 30 | C$_4$ to C$_{26}$[b] |

[a]0.0075 mmol of transition metal compound (pre-catalyst) and 0.35 g of MAO (30 wt % in toluene), Al/M = 240.
[b]After removing all volatiles under vacuum overnight, the mol % of terminal olefins was estimated to be 64% by $^1$H NMR. GC/MS of this fraction showed that it included C$_{18}$–C$_{26}$ olefins.

While certain representative embodiments and details have been shown to illustrate the invention, it will be apparent to skilled artisans that various process and product changes from those currently disclosed may be made without departing from this invention's scope. The appended claims define the invention's scope.

All cited patents, test procedures, priority documents, and other cited documents are fully incorporated by reference to the extent that this material is consistent with this specification and for all jurisdictions in which such incorporation is permitted.

Certain features of the present invention are described in terms of a set of numerical upper limits and a set of numerical lower limits. This specification discloses all ranges formed by any combination of these limits. All combinations of these limits are within the scope of the invention unless otherwise indicated.

We claim:
1. A catalyst precursor compound represented by the formula:
wherein:

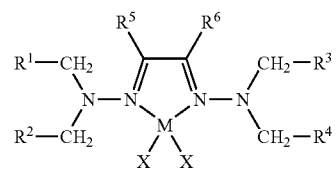

(a) N is nitrogen;
(b) C is carbon;
(c) H is hydrogen;
(d) M is a Group-10 metal;
(e) R$^1$, R$^2$, R$^3$ and R$^4$ are independently hydrocarbyl, substituted hydrocarbyl, halocarbyl, or substituted halocarbyl; or R¹ and R² or R³ and R⁴, independently, are connected to form a heteroalicyclic hydrocarbyl ring structure;

(f) R⁵ and R⁶ are, independently, hydrogen, hydrocarbyl radicals, substituted hydrocarbyl, halocarbyl or substituted halocarbyl radicals; or are connected to form a saturated, partially unsaturated or aromatic ring structure provided they do not form a acenaphthene ring structure; and (g) X are, independently, abstractable ligands.

2. The compound of claim 1 wherein the abstractable ligands are independently one of hydride, hydrocarbyl radicals, or hydrocarbyl-radical-substituted organometalloid radicals.

3. The compound of claim 1 wherein X are independently one of chloride, bromide, iodide, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, hydride, phenyl, benzyl, phenethyl, tolyl, methoxy, ethoxy, propoxy, butoxy, dimethylamido, diethylamido, methylethylamido, phenoxy, benzoxy, or allyl.

4. The compound of claim 1 wherein R¹–R⁶ are independently selected from methyl, ethyl, or all isomers of propyl, butyl, pentyl, hexyl, heptyl, octyl, nonyl, decyl, undecyl, dodecyl, tridecyl, tetradecyl, octacosyl, nonacosyl, triacontyl, cyclohexyl, cyclopentyl, cycloheptyl, cyclooctyl, cyclodecyl, cyclododecyl, naphthyl, phenyl, tolyl, benzyl, and phenethyl radicals.

5. The compound of claim 1 where R¹ is joined to R² and R³ is joined to R⁴ to form a propan-1,3-diyl, butan-1,4-diyl, pentan-1,5-diyl, hexan-1,6-diyl, heptan-1,7-diyl, octane-1,8-diyl, nonan-1,9-diyl, or decan-1,10-diyl fragment, that forms the respective 1-azacyclohexyl, 1-azacycloheptyl, 1-azacyclooctyl, 1-azacyclononyl, 1-azacyclodecyl, 1-azacycloundecyl, 1-azayclododecyl or 1-azacyclotridecyl substituent.

6. The compound of claim 1 where R⁵ and R⁶ are hydrogen, methyl, ethyl or propyl.

7. The compound claim 1 wherein R is joined to R⁶ to form 2,2'-biphenyl, cyclohex-1,2-diyl, cyclopent-1,2-diyl, cyclohept-1,2,-diyl, cyclooct-1,2-diyl, cyclonon-1,2-diyl, cyclodec-1,2-diyl, cyclododec-1,2-diyl, dioxan-1,2-diyl, dithian-1,2-diyl, oxathian-1,2-diyl, piperazin-1,2-diyl, morpholin-1,2-diyl, or thiamorpholin-1,2-diyl.

8. The compound of claim 1 wherein the abstractable ligands are independently hydride radicals; hydrocarbyl radicals; hydrocarbyl-substituted, or organometalloid radicals.

9. The compound claim 1 wherein the abstractable ligands are one of chloride, bromide, iodide, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, hydride, phenyl, benzyl, phenethyl, tolyl, methoxy, ethoxy, propoxy, butoxy, dimethylamino, diethylamino, methylethylamino, phenoxy, benzoxy, allyl, 1,1-dimethyl allyl, 2-carboxymethyl allyl, acetylacetonate, 1,1,1,5,5,5-hexa-fluoroacetylacetonate, 1,1,1-trifluoro-acetylacetonate, or 1,1,1-trifluoro-5,5-di-methylacetylacetonate radicals.

10. A catalyst precursor compound represented by the formula:

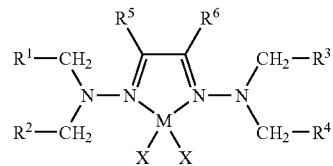

wherein:
(a) N is nitrogen;
(b) C is carbon;
(c) H is hydrogen;
(d) M is nickel or palladium;
(e) R¹ is joined to R² and R³ is joined to R⁴ to form a heteroalicyclic hydrocarbyl ring structure;
(f) R⁵ and R⁶ are independently hydrogen, or a methyl, ethyl or propyl radical; and
(g) X are selected from chloride, bromide, methyl or ethyl.

11. A process for preparing dimers and/or oligomers comprising combining under suitable conditions ethylene, propylene, and/or 1-butene monomer; activator; and one or more catalyst precursor compounds represented by the formula:

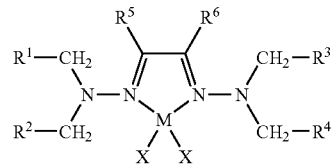

wherein:
(h) N is nitrogen;
(i) C is carbon;
(j) H is hydrogen;
(k) M is a Group-10 metal;
(l) R¹, R², R³ and R⁴ are independently hydrocarbyl, substituted hydrocarbyl, halocarbyl, or substituted halocarbyl; or R¹ and R² or R³ and R⁴, independently, are connected to form an heteroalicyclic hydrocarbyl ring structure;
(m) R⁵ and R⁶ are independently hydrogen, hydrocarbyl radicals, substituted hydrocarbyl, halocarbyl or substituted halocarbyl radicals; and
(n) X are independently abstractable ligands;
and obtaining therefrom a product comprising one or more of 2 to 75 mer unit oligomers.

12. The process of claim 11 wherein the abstractable ligands are independently one of hydride, hydrocarbyl radicals, or hydrocarbyl-radical-substituted organometalloid radicals.

13. The process of claim 11 wherein X are independently one of chloride, bromide, iodide, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, hydride, phenyl, benzyl, phenethyl, tolyl, methoxy, ethoxy, propoxy, butoxy, dimethylamido, diethylamido, methylethylamido, phenoxy, benzoxy, or allyl.

14. The process of claim 11 wherein $R^1$–$R^6$ are independently selected from methyl, ethyl, or all isomers of propyl, butyl, pentyl, hexyl, heptyl, octyl, nonyl, decyl, undecyl, dodecyl, tridecyl, tetradecyl, octacosyl, nonacosyl, triacontyl, cyclohexyl, cyclopentyl, cycloheptyl, cyclooctyl, cyclodecyl, cyclododecyl, naphthyl, phenyl, tolyl, benzyl, and phenethyl radicals.

15. The process of claim 11 where $R^1$ is joined to $R^2$ and $R^3$ is joined to $R^4$ to form a propan-1,3-diyl, butan-1,4-diyl, pentan-1,5-diyl, hexan-1,6-diyl, heptan-1,7-diyl, octane-1,8-diyl, nonan-1,9-diyl, or decan-1,10-diyl fragment, that forms the respective 1-azacyclohexyl, 1-azacycloheptyl, 1-azacyclooctyl, 1-azacyclononyl, 1-azacyclodecyl, 1-azacycloundecyl, 1-azayclododecyl or 1-azacyclotridecyl substituent.

16. The process of claim 11 where $R^5$ and $R^6$ are hydrogen, methyl, ethyl, or propyl.

17. The process claim 11 wherein $R^5$ is joined to $R^6$ to form 2,2'-biphenyl, cyclohex-1,2-diyl, cyclopent-1,2-diyl, cyclohept-1,2,-diyl, cyclooct-1,2-diyl, cyclonon-1,2-diyl, cyclodec-1,2-diyl, cyclododec-1,2-diyl, dioxan-1,2-diyl, dithian-1,2-diyl, oxathian-1,2-diyl, piperazin-1,2-diyl, morpholin-1,2-diyl, or thiamorpholin-1,2-diyl.

18. The process of claim 11 wherein the abstractable ligands are independently hydride radicals; hydrocarbyl radicals; hydrocarbyl-substituted, or organometalloid radicals.

19. The process claim 11 wherein the abstractable ligands are one of chloride, bromide, iodide, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, hydride, phenyl, benzyl, phenethyl, tolyl, methoxy, ethoxy, propoxy, butoxy, dimethylamino, diethylamino, methylethylamino, phenoxy, benzoxy, allyl, 1,1-dimethyl allyl, 2-carboxymethyl allyl, acetylacetonate, 1,1,1,5,5,5-hexa-fluoroacetylacetonate, 1,1,1-trifluoro-acetylacetonate, or 1,1,1-trifluoro-5,5-di-methylacetylacetonate radicals.

20. The process of claim 11 wherein the monomer consists essentially of ethylene.

21. The process of claim 11 wherein the product comprises 2 to 10 mer unit oligomers.

22. The process of claim 11 wherein the product comprises 2 to 6 mer unit oligomers.

23. The process of claim 11 wherein the product consists of essentially 2 to 10 mer unit oligomers.

24. The process of claim 11 wherein the product comprises greater than 90 weight percent oligomers having 2 to 75 mer units.

25. The process of claim 11 wherein the product comprises greater than 90 weight percent oligomers having 2 to 6 mer units.

26. The process of claim 11 wherein the product comprises greater than 95 weight percent oligomers having 2 to 75 mer units.

27. The process of claim 11 wherein the product comprises greater than 95 weight percent oligomers having 2 to 6 mer units.

28. A process for preparing dimers and/or oligomers comprising combining under suitable conditions ethylene, propylene, and/or 1-butene; activator; and one or more catalyst precursor compounds represented by the formula:

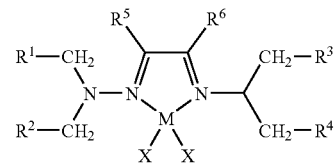

wherein:
(a) N is nitrogen;
(b) C is carbon;
(c) H is hydrogen;
(d) M is nickel or palladium;
(e) $R^1$ is joined to $R^2$ and $R^3$ is joined to $R^4$ to form a heteroalicyclic hydrocarbyl ring structure;
(f) $R^5$ and $R^6$ are independently hydrogen, or a methyl, ethyl or propyl radical; and
(g) X are selected from chloride, bromide methyl or ethyl; and obtaining therefrom a product consisting essentially of one or more of 2 to 75 mer units oligomers.

29. The process of claim 28 wherein the monomer consists essentially of ethylene.

30. The process of claim 28 wherein the product comprises 2 to 10 mer unit oligomers.

31. The process of claim 28 wherein the product comprises 2 to 6 mer unit oligomers.

32. The process of claim 28 wherein the product consists of essentially 2 to 10 mer unit oligomers.

33. The process of claim 28 wherein the product comprises greater than 90 weight percent oligomers having 2 to 75 mer units.

34. The process of claim 28 wherein the product comprises greater than 90 weight percent oligomers having 2 to 6 mer units.

35. The process of claim 28 wherein the product comprises greater than 95 weight percent oligomers having 2 to 75 mer units.

36. The process of claim 28 wherein the product comprises greater than 95 weight percent oligomers having 2 to 6 mer units.

37. The process of claim 28 wherein the suitable conditions comprise a polymerization pressure of 800 psig or less.

38. The process of claim 28 wherein the suitable conditions comprise a polymerization pressure of 500 psig or less.

39. The process of claim 28 wherein the suitable conditions comprise a polymerization pressure of 200 psig or less.

* * * * *